United States Patent
Ramsey et al.

(10) Patent No.: US 10,870,111 B2
(45) Date of Patent: Dec. 22, 2020

(54) FLUIDIC DEVICES WITH BEAD WELL GEOMETRIES WITH SPATIALLY SEPARATED BEAD RETENTION AND SIGNAL DETECTION SEGMENTS AND RELATED METHODS

(71) Applicant: The University of North Carolina at Chapel Hill, Chapel Hill, NC (US)

(72) Inventors: John Michael Ramsey, Chapel Hill, NC (US); William Hampton Henley, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 278 days.

(21) Appl. No.: 15/742,616

(22) PCT Filed: Jul. 19, 2016

(86) PCT No.: PCT/US2016/042913
§ 371 (c)(1),
(2) Date: Jan. 8, 2018

(87) PCT Pub. No.: WO2017/065854
PCT Pub. Date: Apr. 20, 2017

(65) Prior Publication Data
US 2019/0054470 A1    Feb. 21, 2019

Related U.S. Application Data

(60) Provisional application No. 62/195,381, filed on Jul. 22, 2015.

(51) Int. Cl.
*B01L 3/00* (2006.01)
*G01N 35/00* (2006.01)
(Continued)

(52) U.S. Cl.
CPC .. *B01L 3/502761* (2013.01); *G01N 35/00029* (2013.01); *B01J 2219/00317* (2013.01);
(Continued)

(58) Field of Classification Search
None
See application file for complete search history.

(56) References Cited

U.S. PATENT DOCUMENTS 4,978,540 A   12/1990  Lee
6,042,709 A   3/2000   Parce et al.
(Continued)

FOREIGN PATENT DOCUMENTS

CN   1464071      12/2003
CN   101553306    10/2009
(Continued)

OTHER PUBLICATIONS

Berti et al. "Microfluidic-based electrochemical genosensor coupled to magnetic beads for hybridization detection" *Talanta* 77:971-978 (2009).
(Continued)

*Primary Examiner* — Paul S Hyun
(74) *Attorney, Agent, or Firm* — Myers Bigel, P.A.

(57) ABSTRACT

A fluidic device includes a plurality of reaction wells, typically in a dense array, with at least one bead retention segment in fluid communication with and spatially separated from at least one signal detection segment. A respective bead retention segment can be configured to hold a single bead, which can have a reagent attached thereto.

20 Claims, 15 Drawing Sheets

(51) Int. Cl.
C12Q 1/6823 (2018.01)
C12Q 1/686 (2018.01)
(52) U.S. Cl.
CPC ............... B01J 2219/00648 (2013.01); B01J 2219/00702 (2013.01); B01L 2200/0668 (2013.01); B01L 2300/0877 (2013.01); B01L 2300/0893 (2013.01); C12Q 1/686 (2013.01); C12Q 1/6823 (2013.01); G01N 2035/00158 (2013.01)

(56) References Cited

U.S. PATENT DOCUMENTS

| | | | |
|---|---|---|---|
| 6,143,496 | A | 11/2000 | Brown et al. |
| 6,238,874 | B1* | 5/2001 | Jarnagin ............... C12M 41/46 435/29 |
| 6,565,813 | B1 | 5/2003 | Garyantes |
| 6,589,779 | B1 | 7/2003 | McDevitt et al. |
| 8,222,047 | B2 | 7/2012 | Duffy et al. |
| 8,236,574 | B2 | 8/2012 | Duffy et al. |
| 8,846,415 | B2 | 9/2014 | Duffy et al. |
| 9,110,025 | B2 | 8/2015 | Rissin et al. |
| 9,617,589 | B2 | 4/2017 | Ramsey et al. |
| 2002/0102578 | A1 | 8/2002 | Dickinson et al. |
| 2002/0141905 | A1* | 10/2002 | Sha ....................... B01L 3/5025 422/553 |
| 2002/0168757 | A1* | 11/2002 | Kirk ..................... G06T 7/0012 435/288.5 |
| 2003/0017582 | A1* | 1/2003 | Kim .................. B01L 3/502753 435/288.5 |
| 2003/0049620 | A1 | 3/2003 | Lai et al. |
| 2003/0082576 | A1 | 5/2003 | Jones et al. |
| 2004/0014168 | A1 | 1/2004 | Schreiber et al. |
| 2005/0059048 | A1 | 3/2005 | Gunderson et al. |
| 2006/0088857 | A1 | 4/2006 | Attiya et al. |
| 2009/0021401 | A1 | 1/2009 | Williams et al. |
| 2009/0032401 | A1 | 2/2009 | Ronaghi et al. |
| 2009/0146380 | A1 | 6/2009 | Votaw et al. |
| 2010/0137143 | A1 | 6/2010 | Rothberg et al. |
| 2010/0184036 | A1 | 7/2010 | Fu |
| 2010/0248991 | A1 | 9/2010 | Roesler et al. |
| 2010/0255471 | A1 | 10/2010 | Clarke et al. |
| 2010/0317535 | A1 | 12/2010 | Schmidt et al. |
| 2012/0202709 | A1 | 8/2012 | Bergo |
| 2012/0322666 | A1 | 12/2012 | Pham et al. |
| 2014/0323330 | A1 | 10/2014 | Bergo |
| 2015/0151298 | A1 | 6/2015 | Hobbs et al. |

FOREIGN PATENT DOCUMENTS

| | | |
|---|---|---|
| CN | 101848765 | 9/2010 |
| JP | 2003-009890 | 1/2003 |
| JP | 2007-525963 | 9/2007 |
| JP | 2010112839 A | 5/2010 |
| JP | 2010-519896 | 6/2010 |
| JP | 2011196849 A | 10/2011 |
| WO | WO 91/11533 A1 | 8/1991 |
| WO | WO 96/37630 A1 | 11/1996 |
| WO | 9939829 | 8/1999 |
| WO | 9939829 A1 | 8/1999 |
| WO | WO 2005/071056 A1 | 8/2005 |
| WO | 2007092713 | 8/2007 |
| WO | 2009078812 | 6/2009 |
| WO | WO 2012/055069 A1 | 5/2012 |
| WO | WO 2013/176767 A1 | 11/2013 |
| WO | WO 2013/188872 A1 | 12/2013 |

OTHER PUBLICATIONS

Chang et al. "Single molecule enzyme-linked immunosorbent assays: Theoretical considerations" *Journal of Immunological Methods* 378:102-115 (2012).
Dörre et al. "Techniques for single molecule sequencing" *Bioimaging* 5:139-152 (1997).
Handique et al. "Microfluidic flow control using selective hydrophobic patterning" *SPIE* 3224:185-195 (1997).
Henley et al. "Fabrication of Microfluidic Devices Containing Patterned Microwell Arrays" *Analytical Chemistry* 84:1776-1780 (2012).
Hinz et al. "Polymer support for exonucleolytic sequencing" *Journal of Biotechnology* 86:281-288 (2001).
Holmberg et al. "The biotin-streptavidin interaction can be reversibly broken using water at elevated temperatures" *Electrophoresis* 26:501-510 (2005).
Huang et al. "Highly sensitive mutation detection based on digital amplification coupled with hydrogel bead-array" *Chemical Communications* 27:4094-4096 (2009).
International Search Report and the Written Opinion of the International Searching Authority corresponding to International Patent Application No. PCT/US2016/042913 (13 pages) (dated May 12, 2017).
Kalinina et al. "Nanoliter scale PCR with TaqMan detection" *Nucleic Acids Research* 25(10):1999-2004 (1997).
Kan et al. "Isolation and detection of single molecules on paramagnetic beads using sequential fluid flows in microfabricated polymer array assemblies" *Lab on a Chip* 12:977-985 (2012).
Kim et al. "Protein immobilization techniques for microfluidic assays" *Biomicrofluidics* 7(4):041501-1-041501-47 (2013).
Leamon et al. "A massively parallel PicoTiterPlate™ based platform for discrete picoliter-scale polymerase chain reactions" *Electrophoresis* 24:3769-3777 (2003).
Lindström et al. "PCR amplification and genetic analysis in a microwell cell culturing chip" *Lab on a Chip* 9:3465-3471 (2009).
Lizardi et al. "Mutation detection and single-molecule counting using isothermal rolling-circle amplification" *Nature Genetics* 19:225-232 (1998).
Malmstadt et al. "A Smart Microfluidic Affinity Chromatography Matrix Composed of Poly(N-isopropylacrylamide)-Coated Beads" *Analytical Chemistry* 75:2943-2949 (2003).
Margulies et al. "Genome sequencing in microfabricated high-density picolitre reactors" *Nature* 437(15):376-380 (2005).
Nagai et al. "Development of a Microchamber Array for Picoliter PCR" *Analytical Chemistry* 73:1043-1047 (2001).
Osborne et al. "Single-Molecule Analysis of DNA Immobilized on Microspheres" *Analytical Chemistry* 72:3678-3681 (2000).
Rissin, David M. "Single Molecule Detection: Analytical Applications and Fundamental Studies" *Dissertation, Tufts University* (183 pages) (Apr. 2007).
Rissin et al. "Single-molecule enzyme-linked immunosorbent assay detects serum proteins at subfemtomolar concentrations" *Nature Biotechnology* 28(6):595-599 (2010).
Rissin et al. "Simultaneous Detection of Single Molecules and Singulated Ensembles of Molecules Enables Immunoassays with Broad Dynamic Range" *Analytical Chemistry* 83:2279-2285 (2011).
Rissin et al. "Multiplexed single molecule immunoassays" *Lab on a Chip* 13:2902-2911 (2013).
Schroeder et al. "User Configurable Microfluidic Device for Multiplexed Immunoassays Based on DNA-Directed Assembly" *Analytical Chemistry* 81:1275-1279 (2009).
Song et al. "Direct Detection of Bacterial Genomic DNA at Sub-Femtomolar Concentrations Using Single Molecule Arrays" *Analytical Chemistry* 85:1932-1939 (2013).
Tan et al. "Monitoring the Reactions of Single Enzyme Molecules and Single Metal Ions" *Analytical Chemistry* 69:4242-4248 (1997).
Zammatteo et al. "Comparison between Microwell and Bead Supports for the Detection of Human Cytomegalovirus Amplicons by Sandwich Hybridization" *Analytical Biochemistry* 253:180-189 (1997).
Quanterix "Scientific Principle of Simoa (Single Molecule Array) Technology" (2 pages) (2013).
Thermo Scientific "Instructions, StartingBlock Blocking Buffers" (3 pages) (2012).

* cited by examiner

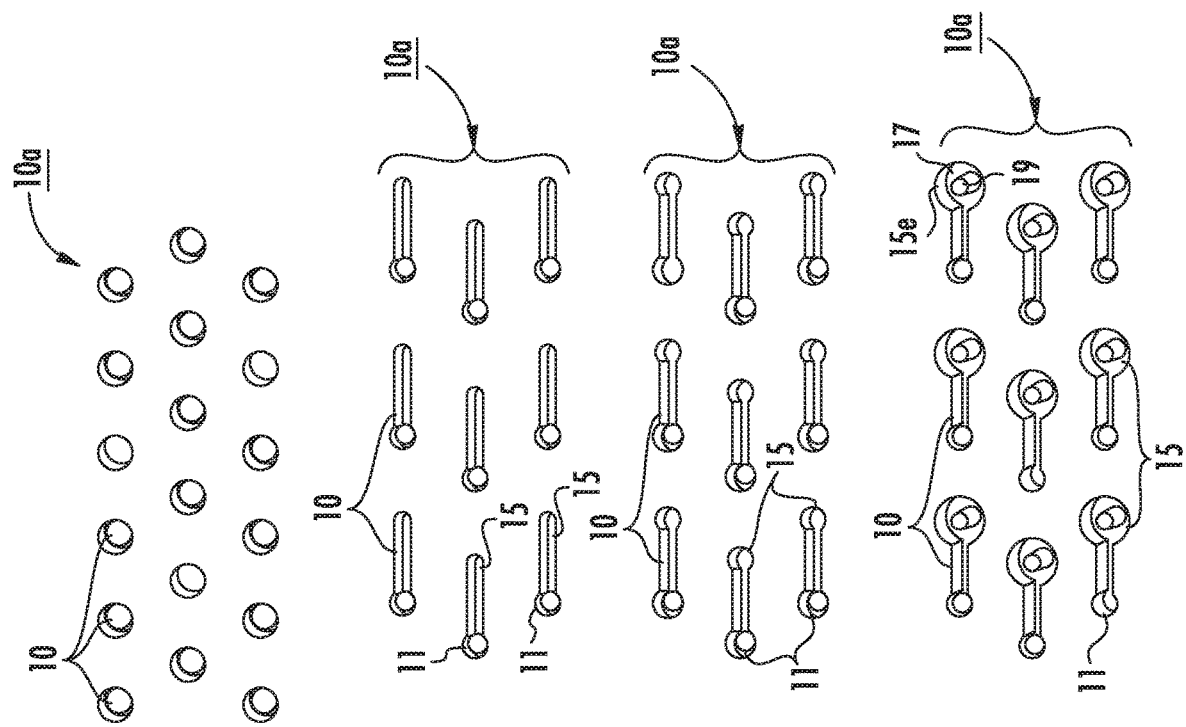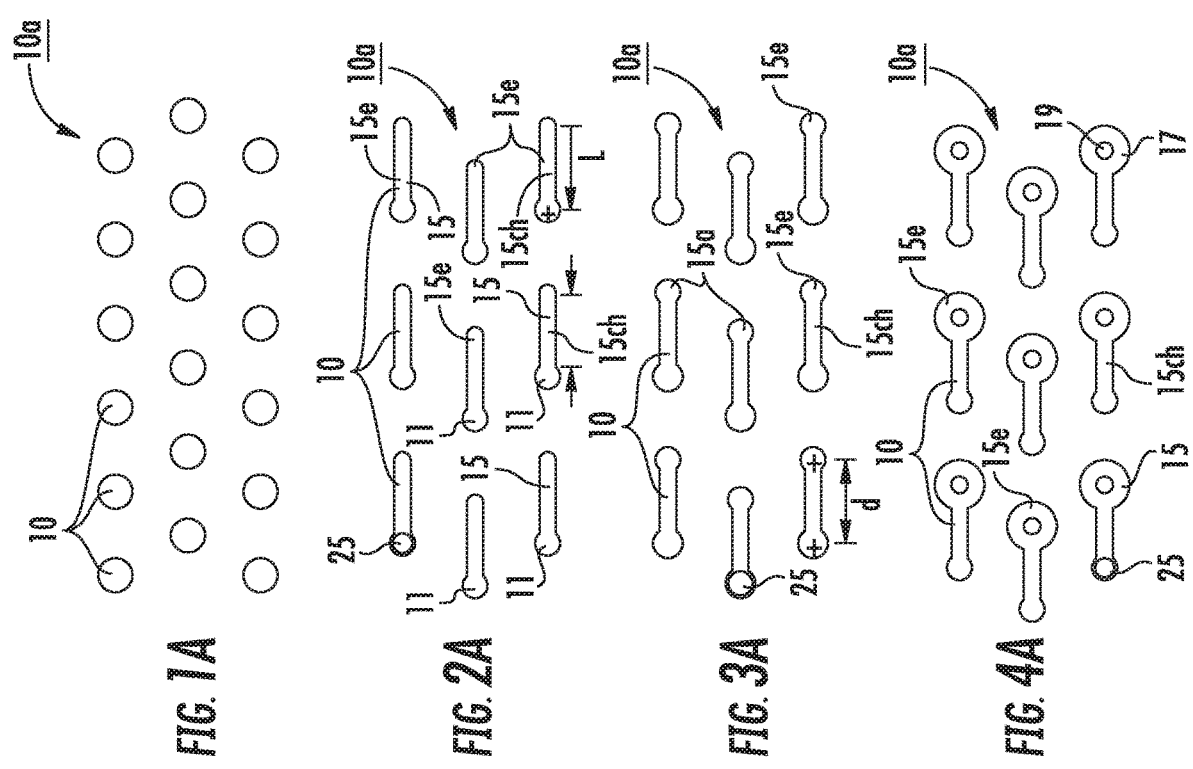

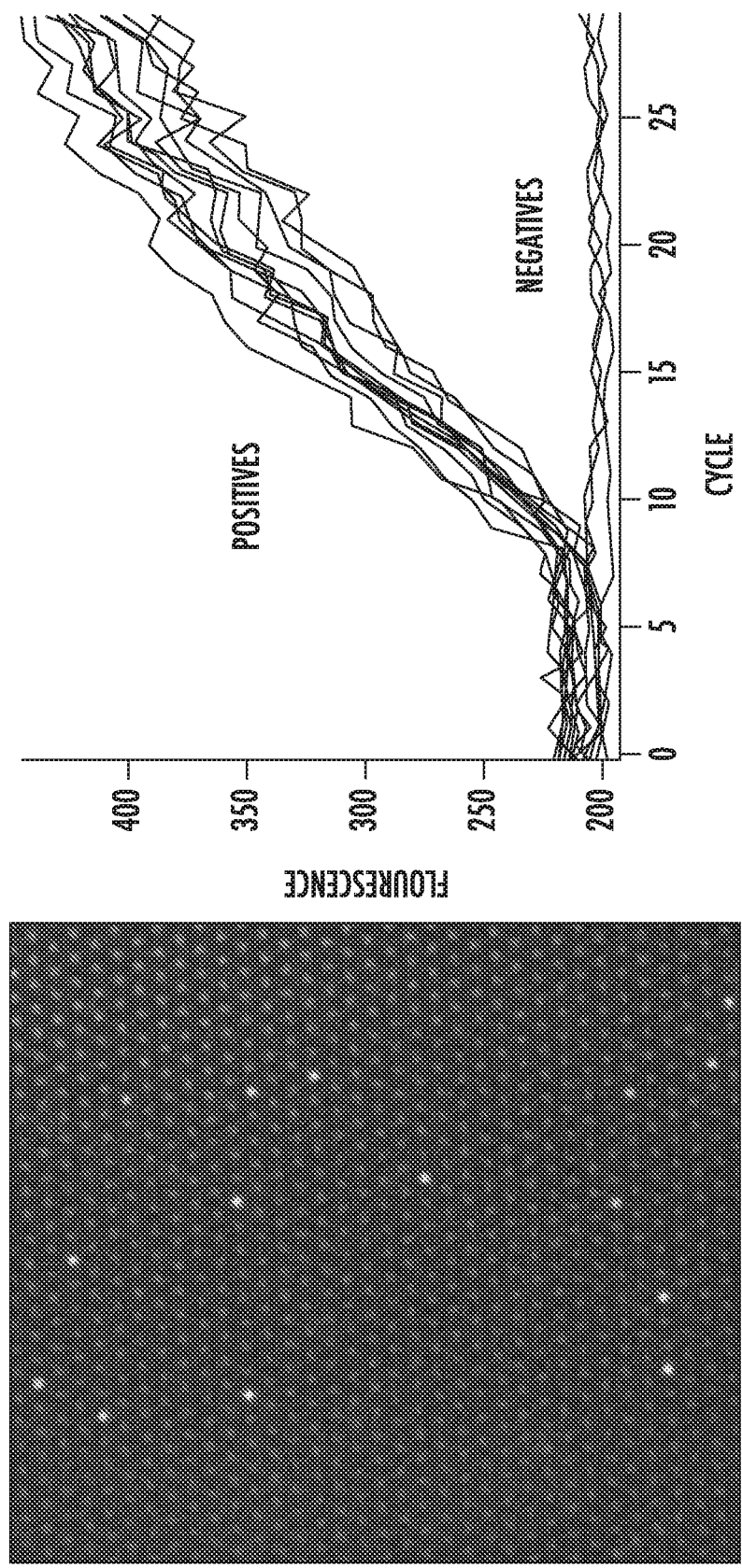

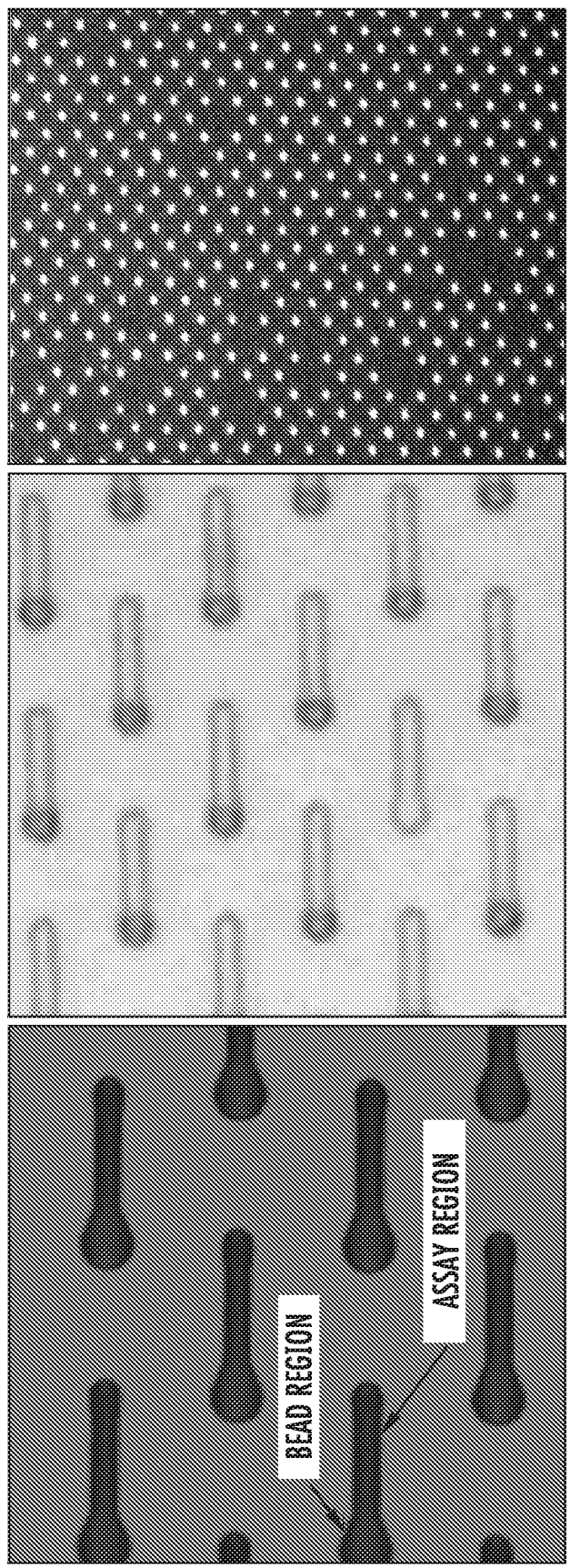

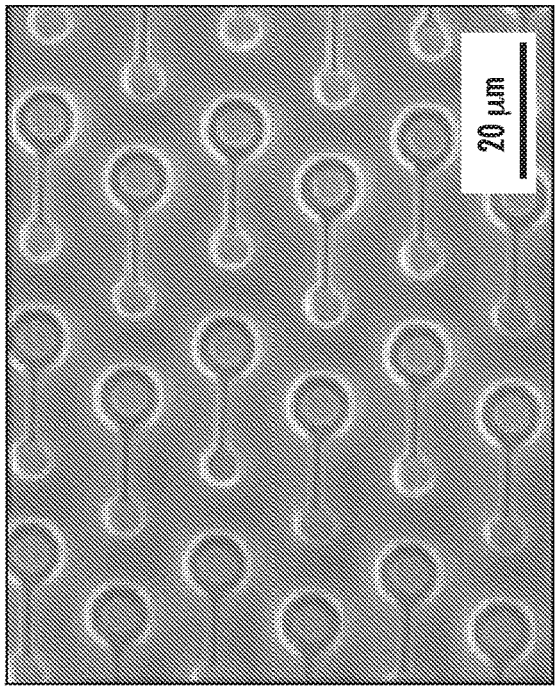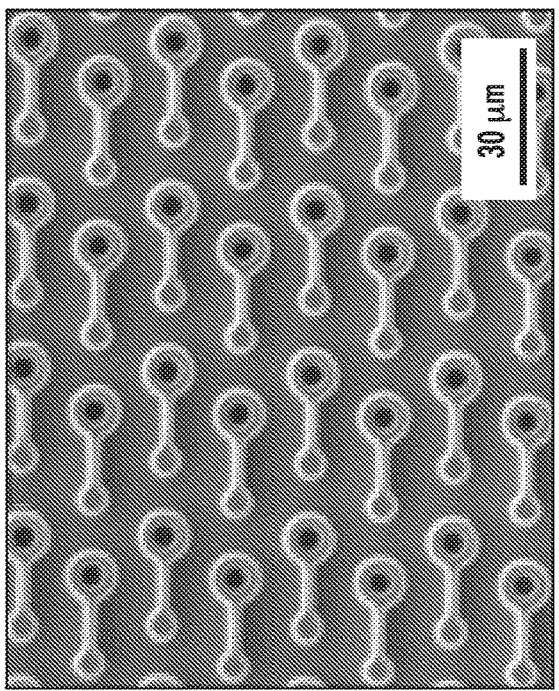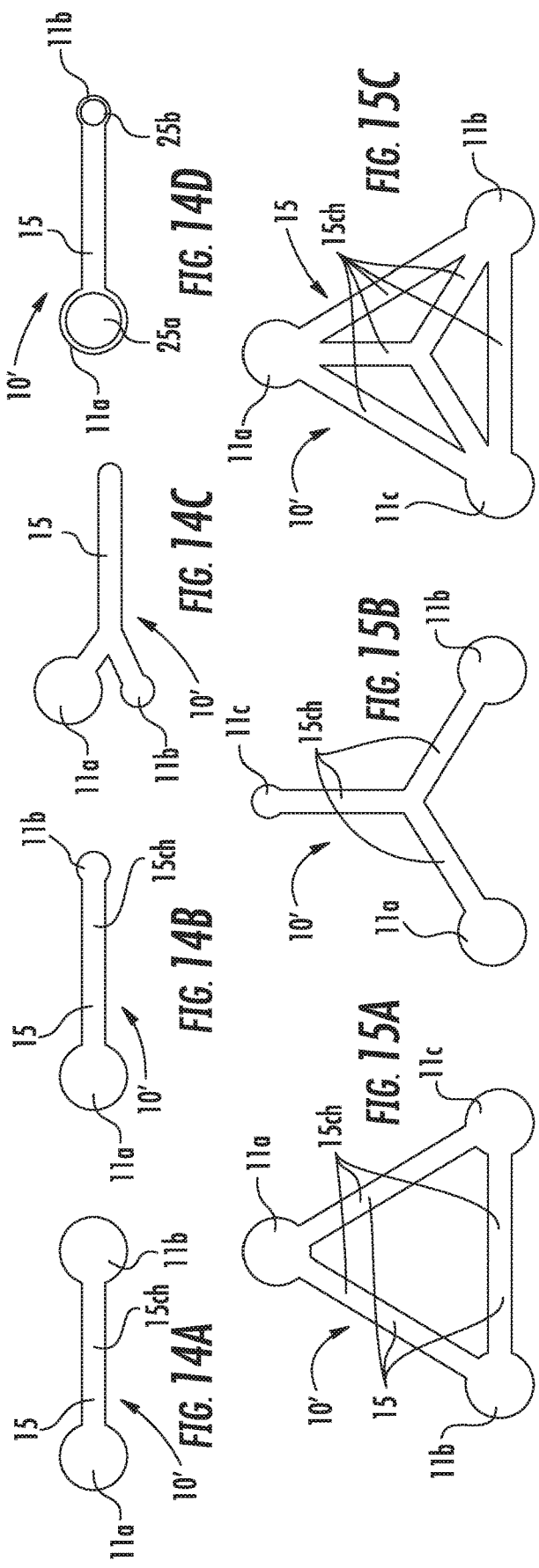

FLUIDIC DEVICES WITH BEAD WELL GEOMETRIES WITH SPATIALLY SEPARATED BEAD RETENTION AND SIGNAL DETECTION SEGMENTS AND RELATED METHODS

RELATED APPLICATIONS

This application is a 35 U.S.C. § 371 national stage application of PCT/US2016/042913, filed Jul. 19, 2016, which claims the benefit of and priority to U.S. Provisional Application Ser. No. 62/195,381, filed Jul. 22, 2015, the contents of which are hereby incorporated by reference as if recited in full herein.

STATEMENT OF FEDERAL SUPPORT

This invention was made with government support under Grant No. HR0011-12-2-0001 awarded by the DOD Defense Advanced Research Projects Agency (DARPA). The government has certain rights in the invention.

FIELD OF THE INVENTION

The present invention relates to fluidic devices.

BACKGROUND

The polymerase chain reaction (PCR) is a highly sensitive method for the amplification of segments of genomic DNA (gDNA) or complementary DNA (cDNA). PCR has many applications, for example, the detection of trace amounts of nucleic acids to determine the presence of disease causing organisms, gene expression, genotyping, genetic engineering or modification, and forensic science applications. PCR amplification provides outstanding target identification and quantification over a large range of analyte concentrations. However, simultaneous and quantitative analysis of many analytes by PCR has proven to be extremely challenging. Intercalating dye fluorescence-based detection is only capable of determining total dsDNA concentration and therefore concurrent analysis of multiple templates in a single reaction vessel is not possible using this detection method. Fluorescent probe technologies (i.e., TaqMan, molecular beacons, or other chemistries) can be used for low-level multiplexing of reactions as each target can be amplified using a different color fluorescence probe as a signaling reporter. Probes are also sequence specific, reducing false positives from primer-dimer formation or nonspecific amplification. A typical method for multiplexing with either conventional microtiter plate or microfluidic real-time-PCR (rt-PCR) is to use a small number of reaction wells, each containing three different color probes. However, it is generally considered challenging to design multiplexed primer and probe sets as they require an additional level of careful design and optimization to insure compatibility with each other. Multiplexing by this method is ultimately limited, by instrumentation and spectral overlap between dyes, to four-color detection, with one color typically reserved for an internal standard dye.

FIGS. 1A and 1B illustrate conventional cylindrical or conical bead wells. The shape and/or limited volume can restrict the solution volume to an area of close proximity to the bead. Bead background fluorescence (significant for polystyrene beads, especially at short wavelengths) or fluorescent dye encoding (used for multiplexed assays) generates a significant background signal that can significantly reduce assay signal to noise. Additionally, some detection dyes bind to the beads and give a high background signal (particularly so in the case of cationic and/or hydrophobic dyes and carboxy-functionalized polystyrene beads). Further, beads may also move an undesired amount in the bead well during an assay readout, making background subtraction of their background fluorescence nontrivial.

SUMMARY OF EMBODIMENTS OF THE INVENTION

Embodiments of the invention provide novel bead well geometries which can separate a respective bead from an adjacent region of solution in the well to enhance signal to noise for assay signal detection in the well.

Embodiments of the invention are directed to a fluidic device that includes a plurality of reaction wells, characterized in that the reaction wells have at least one bead retention segment and at least one spatially separated signal detection segment in fluid communication with the at least one bead retention segment.

The device can be a microfluidic chip and the reaction wells can be provided as an array of reaction wells.

The reaction wells can have a volumetric capacity of between 1 aL to about 1 µL, optionally between about 10 aL to about 1 µL or optionally between about 1 fL to about 1 µL.

The at least one bead retention segment can be sized and configured to hold only a respective single bead.

At least one of the at least one separate signal detection segment can have an end portion that resides a distance L of between 0.3× to about 100× of a diameter of a target bead, typically between 1 to 100 µm, from one or more of the at least one bead retention segment, optionally between 1 to 10 µm.

The at least one bead retention segment can be sized and configured to hold a microspherical bead with a diameter of between about 10 nm to about 1 mm, typically between about 100 nm to about 1 mm.

The at least one bead retention segment can have a width that is between about 101% to about 195% of the diameter of a respective bead held therein.

The separate at least one signal detection segment can include an elongate channel that has a width that is less than a width of an adjacent bead retention segment.

The at least one bead retention segment can be a single bead retention segment.

The at least one bead retention segment can be a plurality of bead retention segments.

The at least one separate signal detection segment can be a plurality of separate signal detection segments. At least one neighboring pair of bead retention segments can be spaced apart by an elongate channel of the at least one signal detection segment. The elongate channel can have a width that is narrower and shallower than a width and depth of the neighboring pair of bead retention segments.

The at least one bead retention segment can be a plurality of bead retention segments, each having a common size.

The at least one bead retention segment can be a plurality of bead retention segments, at least one of which has a different size from at least another one.

A reaction volume of a respective bead well can be between about 2× and 200× greater than a volume of a bead sized and configured to be held by a corresponding bead retention segment.

The bead wells can be provided in a density of between about 6,000 wells/cm$^2$ and about 2,000,000 wells/cm$^2$.

The retention segment and/or the signal detection segment of the bead wells can have tapered and/or straight walls.

One or more of the at least one signal detection segment can have an annular fluid channel spaced a distance apart from the at least one bead retention segment and that is in fluid communication with the at least one bead retention segment.

The bead wells can have first and second spaced apart end portions fluidly connected by a straight fluid channel with a more narrow width.

The first end portion can have a circular perimeter and define a first bead retention segment and the second end portion can have a circular perimeter and define a second bead retention segment.

The first end portion can be larger or smaller in diameter and/or depth compared to the second end portion.

Other embodiments are directed to methods for processing, detecting or analyzing an analyte using the device having any of the above features by electronically detecting an encoded bead signal and/or an assay signal from the at least one signal detection segment of the reaction wells.

The electronically detecting assay signal can be configured to detect a positive assay signal from the at least one signal detection segment of a respective reaction well.

Optionally, the electronically detecting signal can be carried out after a reaction without requiring a baseline readout before the reaction.

Optionally, the electronically detecting signal can be configured to detect an encoded signal from the at least one signal detection segment of a respective reaction well before an assay is carried out.

The electronically detecting signal can be carried out for an array containing more than one type of bead, each bead type encoded with a unique signature (optionally a combination of fluorescent dyes at different intensity levels) and each type functionalized with a different reagent for allowing detection of different analytes or different chemical reactions.

Still other embodiments are directed to methods of fabricating microwells. The methods include forming a plurality of closely spaced apart reaction wells into or onto at least one substrate, the reaction wells having at least one bead retention segment and at least one separate signal detection segment in fluid communication with the at least one bead retention segment. Centerlines of bead retention segments of neighboring reaction wells can be spaced apart a distance of between 1 and 20 μm, and the at least one signal detection segment extends a distance L that is between 0.3× and 100× of a diameter of a target bead, optionally between 1 μm-20 μm or more, typically 1 mm or less, from a centerline of the at least one bead retention segment.

Other embodiments are directed to analysis systems. The systems include a controller, a detector in communication with the controller, and an image processor with a module configured to identify signal present in signal detection segments of a reaction wells of a device holding the reaction wells. The reaction wells have at least one bead retention segment and at least one separate signal detection segment that extends a distance away from the at least one bead retention segment and is in fluid communication with the at least one bead retention segment. The module is configured to identify a positive assay signal associated with a signal detection segment that extends a distance away from the at least one bead retention segment, and optionally wherein the identification is carried out after a reaction without requiring a baseline readout from the detector before the reaction The module can be configured to carry out bead decoding based on identified positive assay signals or before or during when an assay is carried out.

The module can be configured to identify at least two beads held in first and second separate bead retention segments of a single reaction well. The well can have at least one signal detection segment in fluid communication with one or both of the bead retention segments.

Centerlines of bead retention segments of neighboring reaction wells can be spaced apart a distance of between 1 and 20 μm or more.

The at least one signal detection segment can extend a distance L that is between 0.3× and 200× of a diameter of a target bead, optionally between 1-20 μm or more, from a centerline of the at least one bead retention segment of a respective reaction well.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 1A is a top view of a prior art bead well array.

FIG. 1B is a side perspective view of the conventional bead wells shown in FIG. 1A.

FIG. 2A is a top view of an exemplary bead well array according to embodiments of the present invention.

FIG. 2B is a side perspective view of the bead wells shown in FIG. 2A.

FIG. 3A is a top view of another exemplary bead well array according to embodiments of the present invention.

FIG. 3B is a side perspective view of the bead wells shown in FIG. 3A.

FIG. 4A is a top view of yet another bead well array according to embodiments of the present invention.

FIG. 4B is a side perspective view of the bead wells shown in FIG. 4A.

FIG. 7A is a fluorescence microscopy image of a portion of a well array after 30 cycles of PCR.

FIG. 7B is a plot of fluorescence signal from 12 positive and 3 negative reaction wells. The relatively high effective concentration of a 1 copy/50 fL reaction results in an early Ct of ≈11 cycles.

FIG. 8A is a bright field microscopy image of linked bead and reaction wells DRIE in a Si wafer.

FIG. 8B shows a brightfield microscopy image of an array similar to that shown in FIG. 8A and is shown loaded with beads according to embodiments of the present invention.

FIG. 8C is a fluorescence microscopy image illustrating a high background fluorescence of the beads in an array loaded with 3.3 μm diameter Promag beads according to embodiments of the present invention.

FIGS. 13A and 13B are SEM images showing an array fabricated with hot embossing using DRIE etched silicon mold (FIG. 13A) to fabricate bullseye-shaped wells (FIG. 13B) in plastic/polymeric substrates according to embodiments of the present invention.

FIGS. 14A-14D are top schematic illustrations of examples of reaction wells with dual or multi-bead retention geometries according to embodiments of the present invention.

FIGS. 15A-15C are top schematic illustrations of examples of reaction wells with greater than two bead retention geometries according to embodiments of the present invention.

DETAILED DESCRIPTION OF EMBODIMENTS OF THE INVENTION

Figure 5A:
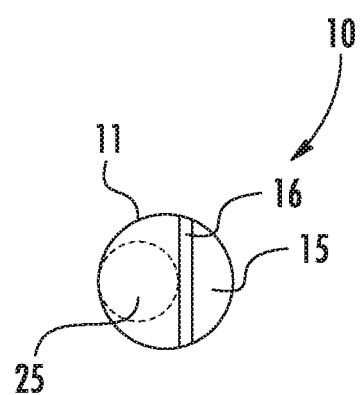
FIG. 5A is a top view of another exemplary bead well with a barrier according to embodiments of the present invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. The abbreviations "FIG. and "Fig." for the word "Figure" can be used interchangeably in the text and figures.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The terms "microchip" and "microfluidic chip" are used interchangeably and refer to a substantially planar, thin device. The microfluidic chip can be rigid, semi-rigid or flexible. The term "thin" refers to a thickness dimension that is 10 mm or less such as between 10 mm and 0.1 mm, and can be about 3 mm, about 2.5 mm, about 2 mm, about 1.5 mm, about 1 mm, or about 0.5 mm. The microchip typically has a width and length that is less than about 6 inches, more typically between about 1 inch and 6 inches. However, in some embodiments, the microchip can be longer such as a foot or more in length and/or width. The microchip can have a width dimension that is less than a length dimension. The microfluidic chip can have a width dimension that is about 2.13 inches (54 mm) and a length dimension that is about 3.4 inches (85.5 mm), in some embodiments. The microchip can include micro-sized and/or nano-sized fluidic channels.

The term "primary dimension" refers to a width and/or depth dimension of a fluidic channel.

The terms "micro-sized" and "microfluidic" with respect to a fluidic channel refer to a fluid flow channel that has sub-millimeter or smaller size width and/or depth (e.g., the term includes micrometer and nanometer size channels) and includes channels with at least a segment having a width and/or depth in a size range of millimeters or less, typically less than 900 microns and greater than 1 nm.

A channel of bead wells of a bead well array can have sidewalls and a floor formed into one or more substrates to have an open top surface and a closed bottom surface with the sidewalls extending therebetween. One or more spacers, top substrates, membranes or covers may be used. The top substrate, membrane or cover can seal, cover or otherwise close the upper surface of a fluidic channel(s) and/or array of reaction wells.

The term "about" refers to parameters that can vary between +/−20% or less, such as +/−10%.

The term "beads" refers to solid phase members such as particles, granules or microspheres, typically magnetic microspheres, that can be porous, superficially porous, or nonporous of material(s) such as polymers, photoresists, plastics, glass, silicon dioxide, metal or semimetal oxides (including but not limited to aluminum oxides, titanium oxides, zirconium oxides or other oxides), quantum dots, metal particles, and the like appropriate for use in the reaction wells.

The term "circuit" refers to an entirely hardware embodiment or an embodiment combining software and hardware.

The analyte in a sample can be any analyte of interest from a sample including, for example, various mixtures including synthetic and biological macromolecules, nanoparticles, small molecules, DNA, nucleic acids/polynucleic acids, peptides, proteins and the like. The analyte can be one or more analyte molecules. The sample or analyte of a sample can include one or more polar metabolites such as amino acids or charged molecules, molecules, peptides, and proteins. The sample and/or analyte may also or alternatively include molecules extracted from biofluids, blood, serum, urine, dried blood, cell growth media, lysed cells, beverages or food. The sample may also or alternatively include environmental samples such as water, air or soil.

The term "oligonucleotide" refers to a nucleic acid sequence of at least about five nucleotides to about 500 nucleotides (e.g., 5, 6, 7, 8, 9, 10, 12, 15, 18, 20, 21, 22, 25, 30, 35, 40, 45, 50, 55, 60, 65, 70, 75, 80, 85, 90, 100, 125, 150, 175, 200, 250, 300, 350, 400, 450 or 500 nucleotides). In some embodiments, for example, an oligonucleotide can be from about 15 nucleotides to about 50 nucleotides, or about 20 nucleotides to about 25 nucleotides, which can be used, for example, as a primer in a polymerase chain reaction (PCR) amplification assay and/or as a probe in a hybridization assay or in a microarray. Oligonucleotides of this invention can be natural or synthetic, e.g., DNA, RNA, PNA, LNA, modified backbones, etc., or any combination thereof as are well known in the art.

Probes and primers, including those for either amplification and/or detection, are oligonucleotides (including naturally occurring oligonucleotides such as DNA and synthetic and/or modified oligonucleotides) of any suitable length, but are typically from 5, 6, or 8 nucleotides in length up to 40, 50 or 60 nucleotides in length, or more. Such probes and or primers may be immobilized on or coupled to a solid support such as a bead, chip, pin, or microtiter plate well, and/or coupled to or labeled with a detectable group such as a fluorescent compound, a chemiluminescent compound, a radioactive element, or an enzyme.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques, or by direct visualization on a gel. The amplified sequence can also be detected by adding an intercalating dye to the reaction mixture and monitoring the fluorescence signal strength, which will be proportional to the total mass of double stranded DNA. Although embodiments according to the present invention are described with respect to PCR reactions, it should be understood that other nucleic acid amplification methods can be used, such as reverse transcription PCR (RT-PCR) including isothermal amplification techniques such as rolling circle amplification or loop-mediated isothermal amplification (LAMP), and nucleic acid sequencing methods may also be used.

DNA amplification techniques such as the foregoing can involve the use of a probe, a pair of probes, or two pairs of probes which specifically bind to DNA containing a polymorphism or mutation of interest, but do not bind to DNA that does not contain the polymorphism of interest under the same hybridization conditions, and which serve as the primer or primers for the amplification of the DNA or a portion thereof in the amplification reaction. Such probes are sometimes referred to as amplification probes or primers herein.

The term "reagent" refers to any substance or compound, including primers, the nucleic acid template and the amplification enzyme, that is added to a system in order to bring about a chemical reaction, or added to see if a reaction occurs. Amplification reagents or reagent refer to those reagents (deoxyribonucleotide triphosphates, buffer, etc.) generally used for amplification except for primers, nucleic acid template and the amplification enzyme. Typically, amplification reagents along with other reaction components are placed and contained in a reaction vessel (test tube, microwell, etc.).

The term "magnetic" as used herein includes ferromagnetic, paramagnetic and super paramagnetic properties.

In general, an oligonucleotide probe which is used to detect DNA containing a polymorphism or mutation of interest is an oligonucleotide probe which binds to DNA encoding that mutation or polymorphism, but does not bind to DNA that does not contain the mutation or polymorphism under the same hybridization conditions. The oligonucleotide probe is labeled with a suitable detectable group, such as those set forth below. Such probes are sometimes referred to as detection probes or primers herein.

Referring to FIGS. 2A, 2B, 3A, 3B, 4A and 4B, examples of bead wells 10 with geometries for improved signal detection are shown. As shown in FIGS. 1A and 1B, conventional bead wells 10 have circular perimeters (typically cylindrical or conical wells) that are configured to hold a bead. In contrast, bead wells 10 according to embodiments of the present invention have geometries with a bead retention segment 11 in fluid communication with a signal detection segment 15 that is adjacent the bead retention segment 11.

The bead wells 10 can be provided in a relatively dense array 10a of closely spaced apart bead wells 10. The bead wells 10 can be aligned in rows and columns or be offset from each other. The wells 10 can be provided in a regularly repeating pattern, an irregular repeating pattern, or in other patterns. The term "dense" means that a footprint of a fluidic analysis device can have between about 100-6000 wells 10 per $mm^2$ and/or between 10,000 to 5,000,000 wells 10 per $cm^2$, typically between about 6,000 to about 2,000,000 wells 10 per $cm^2$, more typically between about 500,000 to about 2,000,000 wells 10 per $cm^2$.

Some or all of the neighboring wells 10 can have a separation distance of between 1 μm-10 mm, such as about 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 100 μm, 200 μm, 300 μm, 400 μm, 500 μm, 600 μm, 700 μm, 800 μm, 900 μm, 1 mm, 2 mm, 3 mm, 4 mm, 5 mm, 6 mm, 7 mm, 8 mm, 9 mm, 10 mm, or even greater and any fractional number therebetween, measured centerline to centerline of respective neighboring bead retention segments 11.

Some or all of the wells 10 can all be reaction wells 10 that cooperate with amplification reagents. Some or all of the wells 10 can process sub-pL reaction volumes.

The signal detection segment 15 can optionally comprise a short and/or elongate fluidic channel 15ch that connects an end of the signal detection segment 15e with the bead retention segment 11. The signal detection segment 15 can include an end 15e that is spaced apart a distance "L" from the bead retention segment 11, typically by between 30% to about 10,000% (0.3× to about 100×) of a diameter of a target bead, more typically between about 0.3× to about 20× of the diameter of a target bead. In some embodiments, L can be between 1× and 5× the diameter of a target bead. For example, for 3.2 μm diameter beads, the length L can be between about 1 to about 640 μm, more typically between 1 and 32 μm, and in particular embodiments can be between about 3.2 and 16 μm. To be clear, a number with the letter "X" refers to a multiplier, one times (1×), ten times (10×) and the like.

In some embodiments, L can be between about 1 μm to 10 mm or more, typically up to about 1 mm or about 100 μm, more typically between 1 and 20 μm, such as about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, about 15 μm, about 16 μm, about 17 μm, about 18 μm, about 19 μm, and about 20 μm. The length L can be measured from a centerline of the bead retention segment 11 or from a line completing the diameter of the bead retention segment drawn over the channel 15c connecting the bead retention segment 11 with the end of the signal detection segment 15e.

FIGS. 2A and 2B illustrate that the signal detection segment 15 can be configured as a narrow channel or "slit", typically having a width that is 25%-75% less than a width of the bead retention segment 11.

FIGS. 3A and 3B illustrates that the signal detection segment 15 can have an end portion that is arcuate 15a, with a radius of curvature less than that of the bead retention segment 11. The distance "d" between centerlines of the bead retention segment and the arcuate end 15e can be the same as the length "L" discussed above.

FIGS. 4A and 4B illustrate that the signal detection segment 15 can have an end that has an annular channel 17 surrounding an internal upwardly projecting member 19. The projecting member 19 can have a height sufficient to extend above the fluid in the annular channel 17 of the signal detection segment 15. This configuration can define an optically detectable signal comprising a portion with an annular shape.

The new geometries of the bead wells 10 are believed to improve detection in microbead array-based technologies. These well geometries can be configured such that one area of the well 11 is for magnetic loading and bead retention, and another region of the well 15 can be used (primarily or only) for detection of a signal. In some embodiments, after loading the beads 25 (shown by way of example with a solid circle in one of the wells in each of FIGS. 2A, 3A and 4A) in the bead regions 11 of the wells 10, a small volume of reagent fluid can be isolated in the wells 10 using a method such as immiscible fluid sealing or pushing against another surface such as a gasket or other substrate as is known to those of skill in the art.

While some exemplary embodiments are shown in FIGS. 2A, 2B, 3A, 3B, 4A and 4B, other embodiments may include other geometries, typically configured so that the bead retention region 11 has a pocket or receptacle with an opening diameter that is between about 101-195% of the diameter of the bead 25, and may be between about 105% and 150% in some embodiments. The depth of the well in the bead retention region 11 can be between about 50% and 185% that of the bead diameter.

Figure 5B:
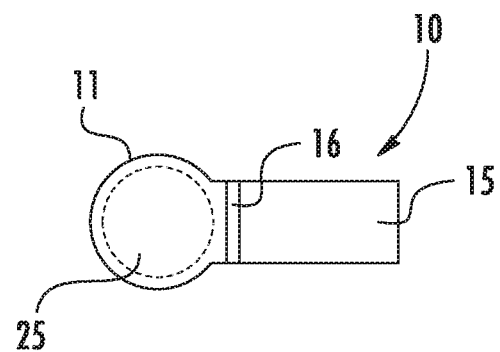
FIG. 5B is a top view of yet another exemplary bead well with a barrier according to embodiments of the present invention.

FIGS. 5A and 5B illustrate the wells 10 can include a physical barrier 16 that can block the bead 25 in the bead retention segment 11. The barrier 16 can allow fluid to enter the signal detection segment 15 from the bead retention segment. The barrier 16 can reside across a top surface, extend down a distance toward a bottom of the well 10 and/or be submerged under fluid levels in the well while inhibiting or preventing the bead 25 from migrating away from the retention region 11. The barrier 16 can extend totally or partially across opposing sidewalls of a reaction well 10.

The depth of the well 10 at the some or all of the signal detection region 15 may be the same, deeper or more shallow than the well at the bead retention segment 11. The depth may decrease as the channel 15ch travels away from the bead retention segment 11. The depth may increase as the channel 15ch travels away from the bead retention segment 11 toward the end of the signal detection segment 15. The walls of the well 10 may taper outwardly or inwardly in a direction into the well 10.

Different wells 10 may have different volumetric capacities, geometrical shapes patterns and/or sizes.

In some embodiments, the signal detection segment or region 15 can have a channel 15ch such as a pocket or slit or other geometric shape into which a target bead cannot physically enter. Both regions 11, 15 are fluidically connected so that reagents and/or analytes released from the bead 25 can diffuse or otherwise mix throughout the common solution volume of the well 10. By spatially separating the bead 25 from the detection region 11, the contribution of bead fluorescence to the signal can be reduced or eliminated, improving signal to noise ratio.

The geometries of the wells 10 can allow high, single occupancy loading of reaction wells 10 while increasing a respective reaction volume, potentially improving reaction efficiency.

As illustrated in FIGS. 6A-6E, a microfluidic device 50 may include a well array 10a with a plurality of wells 10. The wells 10 can hold beads 25 in the bead retention segments 11. The beads 25 can optionally comprise primers attached thereto and may optionally be pre-loaded into the bead retention segments 11 of the wells 10. The device 50 may comprise upper and lower substrates 50u, 50b (FIGS. 6B, 6C) that attach together. The upper substrate 50u may be the same or different from the lower substrate 50b. Either or both substrates 50u can be rigid and comprise glass, quartz, silicon, or a suitable metal for example. Either or both substrates 50b may be polymeric, such as silicone or other polymeric material (such as PMMA, COC, COP, PDMS, PP, PE, PTFE, or Kapton (polyamide), among many others), and it can provide the array of bead wells 10a. The upper or lower substrate 50u can have at least one port 50p in fluid communication with the wells 10. The reaction wells 10 can optionally be perpendicular to flow through the array chamber with the array of wells 10a during reagent filling and/or oil sealing, for example; however, other alignment configurations may be used.

Figure 6A:
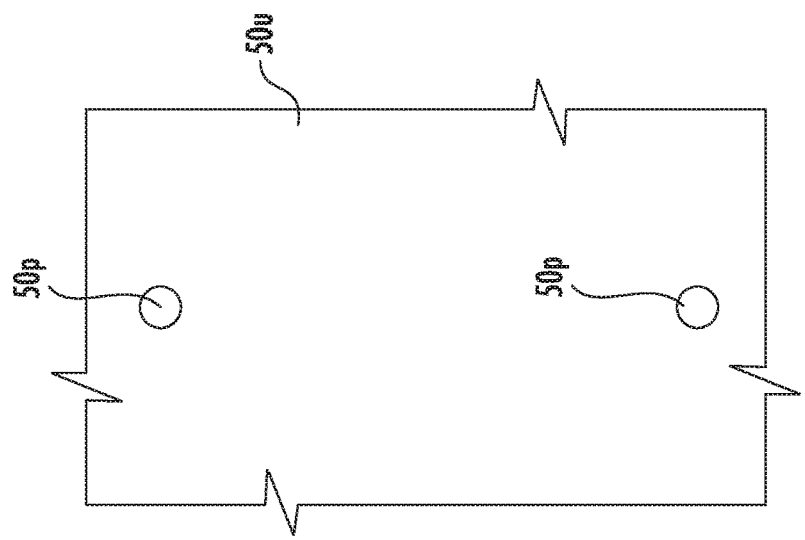
FIG. 6A is a top view of an exemplary microfluidic chip according to embodiments of the present invention.
Figure 6B:
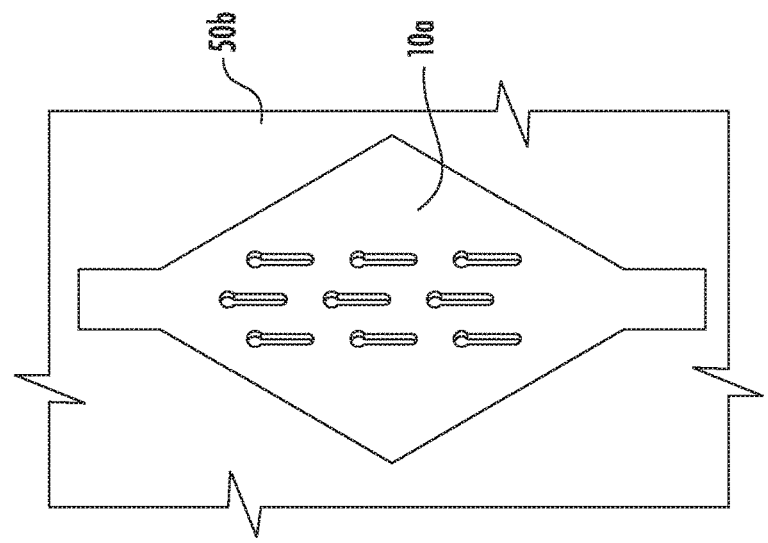
FIGS. 6B and 6C are top views of exemplary attachable substrates for the microfluidic chip shown in FIG. 6A according to embodiments of the present invention.
Figure 6C:
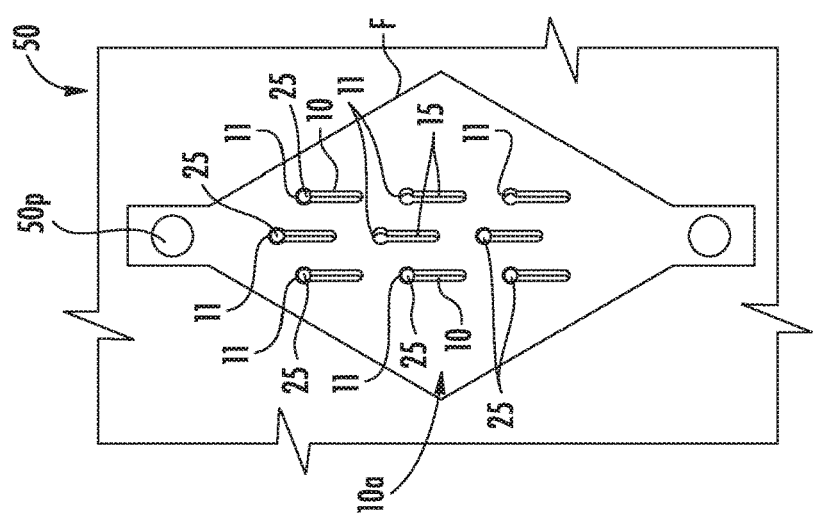

FIG. 6A shows that the microfluidic chip 50 can be configured so that the array of bead wells 10a occupy a footprint "F" (typically between 1 mm and 10 cm) with a dense array wells. The fluidic microchip 50 can include transport channel(s) for a sample and reagents or other chemical additions that can be in fluid communication with the array 10a as is well known to those of skill in the art.

Figure 6D:
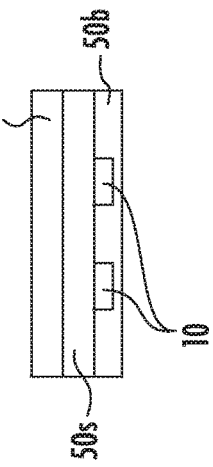
FIG. 6D is a sectional view of a microfluidic chip illustrating an optional spacer according to embodiments of the present invention.

FIG. 6D illustrates an optional spacer 50s that may reside between the upper and lower substrates 50u, 50b. The spacer 50s can define sidewalls of some or all of a respective well 10. The spacer 50s can comprise a photoresist used as both a gasket and spacer.

Figure 6E:
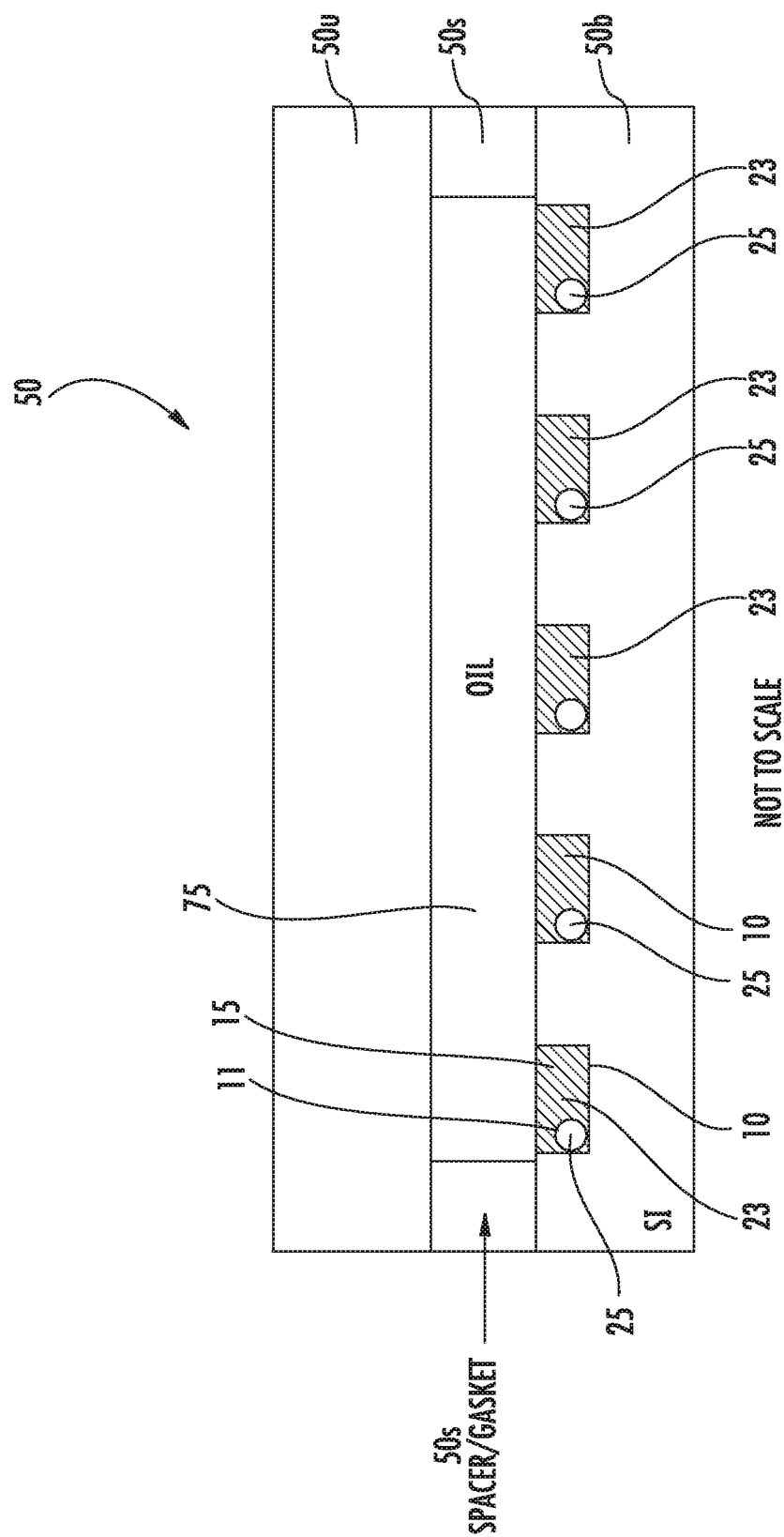
FIG. 6E is a section view of an exemplary microfluidic chip illustrating the use of a sealing agent between adjacent reaction wells according to embodiments of the present invention.

FIG. 6E illustrates that a sealing agent 75 such as sealing oil can separate adjacent wells 10 with beads 25 as is well known to those of skill in the art. Hydrophobic membrane(s) may also or alternatively be used. The sealing agent 75 (e.g., oil) can extend over the top of the bottom substrate 50b. The sealing agent 75 can have a thickness or depth associated with the spacer/gasket 50s. The sealing agent 75 and can cover everything but the bead/reaction well 10. The sealing agent 75 can comprise mineral, silicone, hydrocarbon or fluorocarbon-based oil and/or waxes or any combination or mixture thereof. The reaction solution 23, e.g., an aqueous solution, does not typically touch the top substrate 50u.

This technology may be particularly advantageous for bead-based assays involving amplification methods such as the polymerase chain reaction (PCR) or enzyme-link immunosorbent assays (ELISA) that use fluorescence signal readout in analog or digital detection modes. In these assays, zero, one, or multiple analyte molecules are captured by a magnetic bead. The magnetic bead can then be loaded into a microwell array 10a with a geometry that restricts the loading of the beads 25 to one or zero beads per well 10. A small volume of amplification reagents can be sealed in each reaction well 10 with the bead 25, and a chemical reaction can be performed to produce a fluorescence signal if the analyte molecule is present. The assay fluorescence signal can then be measured, processed, and used to determine analyte concentration in the sample.

Singleplex Reactions in a Compact Array (SiRCA) is a massively parallel amplification and detection method using a microbead-array format that has the potential to perform, hundreds, or thousands to millions of isolated, singleplex rt-PCR reactions for many different target sequences simultaneously. See, e.g., U.S. patent application Ser. No. 14/402,565, describing, for example, bead-based delivery of reagents for parallel assays on a multiplexed-in-space microfluidic device; the contents of this document are hereby incorporated by reference as if recited in full herein.

The ability to perform single copy, digital quantification at low analyte concentrations and multiple copy, analog rt-PCR quantification at high analyte concentrations gives a large dynamic range with aM LODs. In some embodiments, the arrays 10a can be used with individual sets of biotinylated primers that are attached to dye encoded, streptavidin-labeled, magnetic microspheres or beads. A bead set library containing up to tens to hundreds of bead types can be made, each with a different primer set for a different target sequence, and new bead sets can be added to the bead mixture at will. When the bead mixture is incubated with analytes DNA or RNA, the primers attached to the beads act as hybridization probes, capturing and purifying the nucleic acid sequence specific to that bead. Sample matrix interferents (extraneous DNA, RNA, cell membrane components, etc.) can be removed by separating the beads magnetically and washing. After cleanup, polymerase, dNTPs, and intercalating dye are added, and the beads are loaded into individual wells 10 and sealed from one another using an immiscible oil or hydrophobic membrane. Stochastically loading individual, encoded primer beads into separate microreaction wells can be accomplished in a matter of seconds to minutes, unlike hand pipetting or reagent printing. Magnetic loading of beads into optimized geometries can be more efficient than random isolation by dilution into droplets or reaction wells that do not contain regions designed for bead capture and/or a separate detection region for a well 10. The streptavidin/biotin interaction is very stable at temperatures below 50° C.; however, elevated temperatures used for denaturation during PCR may allow the subsequent release of the primers during the first rt-PCR cycle initiating amplification of target DNA.

In order to evaluate the performance of SiRCA in sub-pL reactions, preliminary testing without beads using primers and gDNA was performed in silicon fluidic chips with arrays of wells 3.7 µm in diameter, 5 µm deep (cylindrical with volume ≈50 fL) with a center-to-center spacing of 10 µm, fabricated by deep reactive ion etching (DRIE) in silicon. Thus, the rt-PCR performed in ≈50 fL cylindrical reaction wells with primers and gDNA free in solution without beads. Chips were pretreated with octyltrichlorosilane in heptane to render the surfaces hydrophobic. The chips were wet with ethanol, then water, and then blocked with loading buffer (20 mM Trizma, 50 mM KCl, 2.5 mM $MgCl_2$, 1% BSA, and 0.1% Tween 20). Master mix (1x Platinum Quantitative PCR SuperMix-UDG with 0.0625 units/4 additional Platinum Taq DNA polymerase, 0.5% BSA, 2.7 µM primers, gDNA from *S. mutans*, and 3xSYBR Green) was added to the chip and then Krytox GPL104 perfluorinated oil was pulled through the chip to seal the reaction volumes from one another. FIG. 7A is a fluorescence microscopy image that shows the chip after 30 PCR cycles, and FIG. 7B shows a plot of fluorescence signal for 12 positive wells and 3 negative wells. The relatively high concentration of template associated with one copy per well (1 copy/50 fL or ≈3 µM) results in a Ct of only 11 cycles.

The background fluorescence of polystyrene beads can become more problematic as the reaction well diameter decreases. In previous work using 4-25 pL SiRCA reactions, the reaction-well diameter was approximately 25-50 µm, much larger than the 3.3 µm diameter of the bead (bead volume ≈20 fL). Since the bead well was located in the center of the well, the bead background fluorescence could be ignored or subtracted as background signal. For high-density arrays of sub-pL reactions, the cylindrical bead well is effectively the reaction well, and bead fluorescence can dominate the signal. The bead background fluorescence photobleaches during the imaging of the array, leading to a net decrease in signal regardless of the fluorescence signal generated by PCR amplification. Additionally, during preliminary investigations of sealing and thermocycling beads in small volume wells, under a certain size, e.g., ≈4.5 µm diameter, ≈5 µm deep, the beads were observed to move in the wells between cycles, making background subtraction difficult.

The autofluorescence of polystyrene beads is high at an optimal excitation/emission of about 497 nm/520 nm of SYBR Green, an intercalating dye that provides the assay signal in the presence of double stranded DNA amplicons. Additionally, SYBR Green can interact with the beads, and can cause a considerable increase in bead fluorescence. Other intercalating dyes with excitation/emission maxima of longer wavelengths were tested to try to reduce the contribution of bead background fluorescence to the assay signal, but they failed to produce a stronger fluorescence signal than that observed with SYBR Green at concentrations of 1x-15x. The use of devices that can spatially separate assay signal from the bright background of the bead can be desirable.

Non-cylindrical reaction well geometries were evaluated for use in SiRCA to avoid bead background fluorescence and increase reaction volume. FIG. 8A is a bright field microscopy image of linked bead and reaction wells DRIE in a Si wafer. The bead well segment on the left-hand side of the well is ≈3.5-3.7 µm in diameter; the detection well segment on the right-hand side is ≈2.1 µm diameter. The channel linking them is ≈2.0-2.1 µm wide and 7.4 µm long. The depth can be about ≈5 µm, providing a reaction volume of approximately 150 fL. FIG. 8B illustrates a similar array that is shown loaded with beads. FIG. 8C is an image illustrating a high background fluorescence of the beads in an array loaded with 3.3 µm diameter Promag beads. High occupancy is seen with magnetic loading, and relatively few instances of double loading were observed. The high background fluorescence of the beads is evident.

The new reaction wells 10, 10' can address the problem of bead background fluorescence. Designs that provide sufficient reagent volume for efficient PCR, maintain a high reaction well density for a compact array, and physically separate the bead and its fluorescence signal from a detection region were evaluated. The bead well retention segment 11 can fluidly connect to a channel 15*ch* that is a narrow slit (FIG. 8A). The bead well retention segment 11 can be slightly larger than the bead diameter, and the detection slit can be smaller than the bead diameter, permitting the loading of a single bead per well structure. FIG. 8B shows a brightfield microscopy image of 3.3 µm Promag beads loaded into the wells using magnetic loading techniques such as described in U.S. patent application Ser. No. 14/402, 565, incorporated by reference herein.

Although the detection slit reduces the number of isolated reaction wells that can fit into a given footprint, typically by a factor of 2, the high loading occupancy maintains a high density of loaded wells for a given footprint (>6 k/mm² or 600 k/cm² in this example). Optimization can be performed to determine the optimum well spacing for sealing of reactions, most likely resulting in a higher well density. Relatively few instances of double loading were observed, but due to bead heterogeneity, some smaller beads occasionally loaded into the detection well or connecting slit. This is easily detected, and those wells can be excluded from analysis. Prototypes were fabricated with wells with reaction volumes ranging from ≈100 to 150 fL, with the beads displacing approximately 20 fL.

Figure 9B:
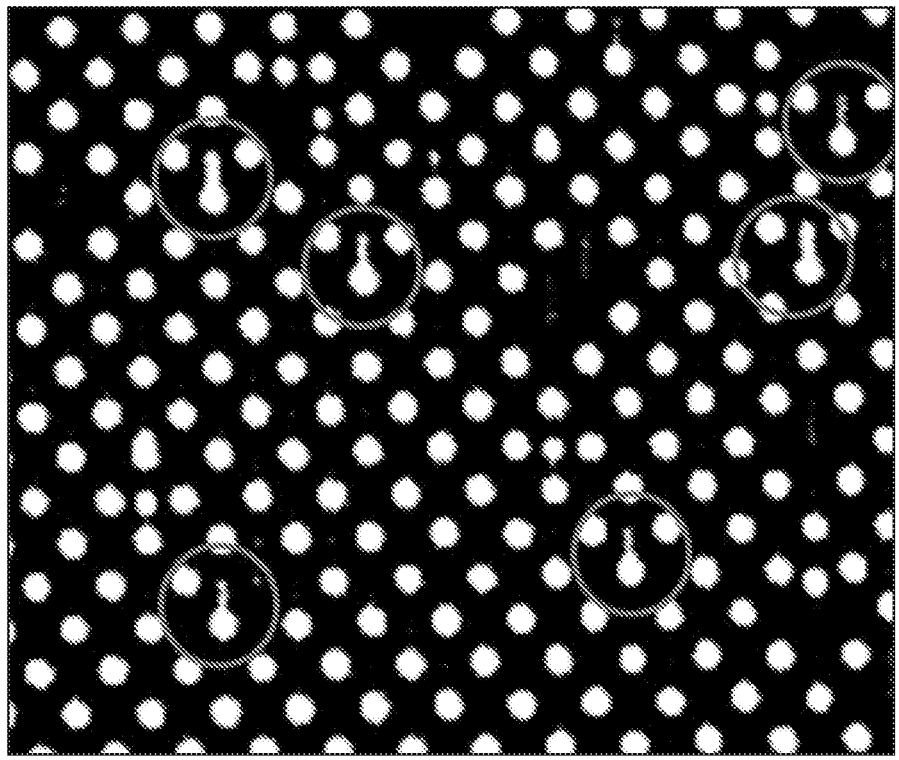
FIGS. 9A and 9B are fluorescence images from cycle 10 (before amplification was detected, FIG. 9A) and cycle 30 (after amplification, FIG. 9B) according to embodiments of the present invention.
Figure 9A:
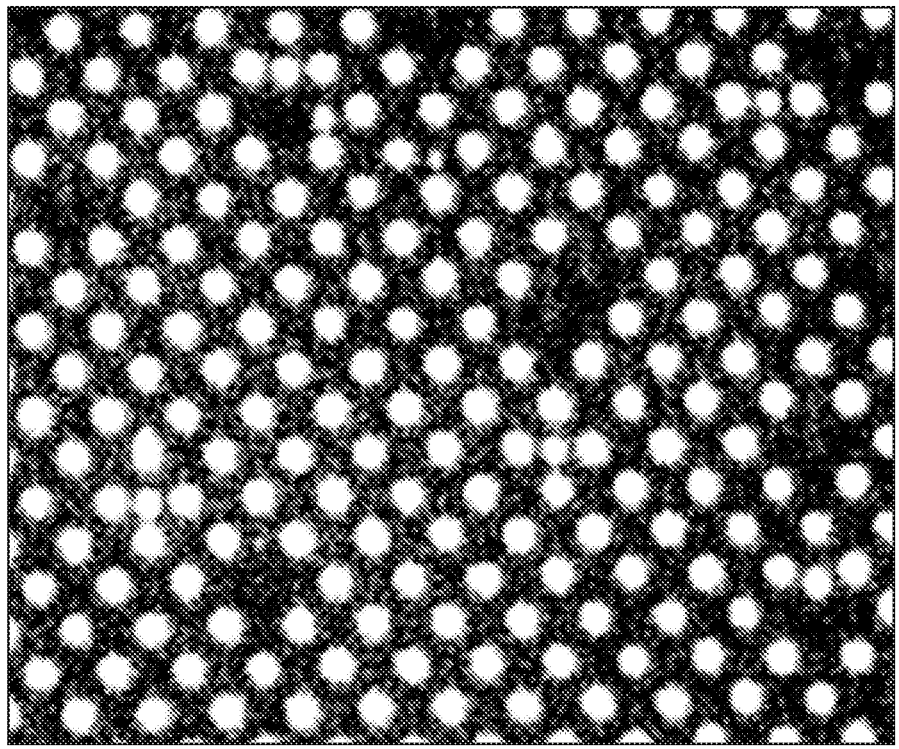

SiRCA was tested in these wells using streptavidin-coated Promag beads functionalized with primers for the 18S rRNA gene conserved between *Plasmodium* species. Briefly, ≈350k primer-labeled beads were incubated for 30 min in 40 µL of a nucleic acid extraction from a malaria blood sample at a concentration ≈4 k parasites/µL at the time of incubation. The beads were washed, and an aliquot was loaded into the chip. Master mix (Kapa SYBR FAST with 1x additional SYBR Green, 0.5% BSA, and 0.125 units/µL of Platinum Taq polymerase) was added to the chip and sealed with Krytox GPL104 oil. FIG. 9A/9B show fluorescence images from cycle 10 (before amplification was detected) and cycle 30 (after amplification). Positive wells are shown circled in FIG. 9B.

SiRCA was performed in devices with non-cylindrical bead wells with reaction volumes of ≈150 fL. A comparison between cycle 10 (FIG. 9A) and cycle 30 (FIG. 9B) is shown, and positive wells (circled with visual "tails" in FIG. 9B) can be identified by an increase in fluorescence in the slit and smaller well. Wells that load more than one bead can be easily identified and discarded from analysis.

Figure 10B:
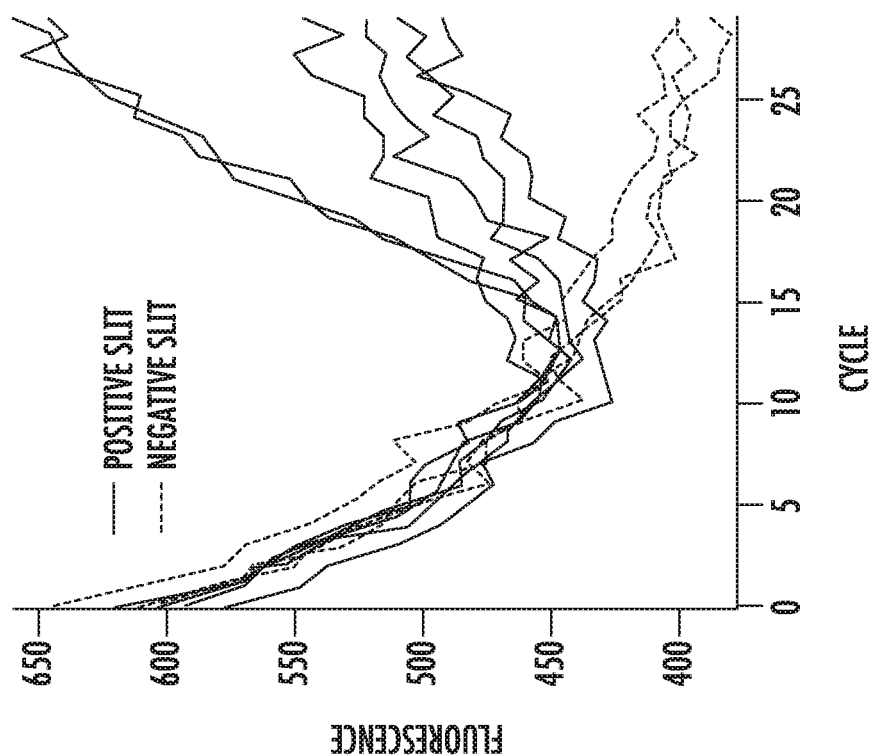
FIG. 10B is a plot of raw fluorescence signals averaged from only the signal detection segment (slit) well regions for these same beads according to embodiments of the present invention.
Figure 10A:
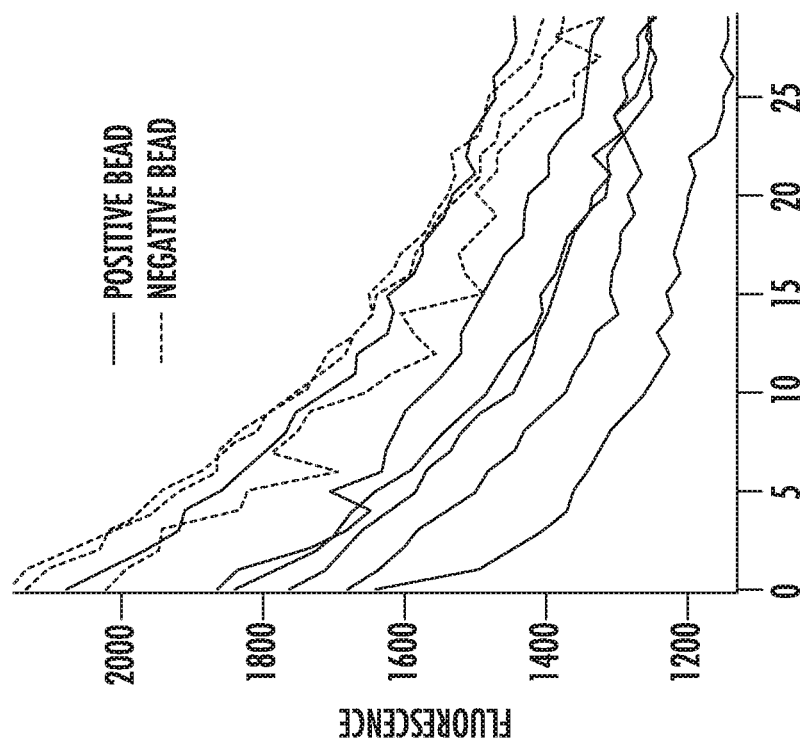
FIG. 10A illustrates a plot of raw fluorescence signals averaged over the bead well regions only for the six positive wells (solid line traces) and three negative wells (dashed line traces) for 30 cycles of rt-PCR.

The ability to read the assay signal in a space away from the bead's background fluorescence makes SiRCA possible in sub-pL wells using SYBR Green. This is illustrated by comparing the average signal from the bead well region with that from the slit and detection well. FIG. 10A shows the average fluorescence signal from only the bead well region for six positive wells and three negative wells shown in FIG. 9B. No difference is readily visually discernible between the negative and positive wells due to the high background signal of the beads. If the signal from only the slit (detection) regions of the wells are plotted (FIG. 10B), the positive reaction wells can be easily distinguished from the blanks by a marked increase in fluorescence signal after approximately 15 cycles of PCR. Photobleaching can be seen for all areas. Modifications to the chip surface and/or buffer or signal processing corrections may reduce the high background in the detection regions in earlier cycles.

FIG. 10A illustrates a plot of raw fluorescence signals averaged over the bead well regions only for the six positive wells (solid traces) and three negative wells (dashed line traces) for 30 cycles of rt-PCR. FIG. 10B is a plot of raw fluorescence signals averaged from only the slit and detection well regions for these same beads.

Figure 11A:
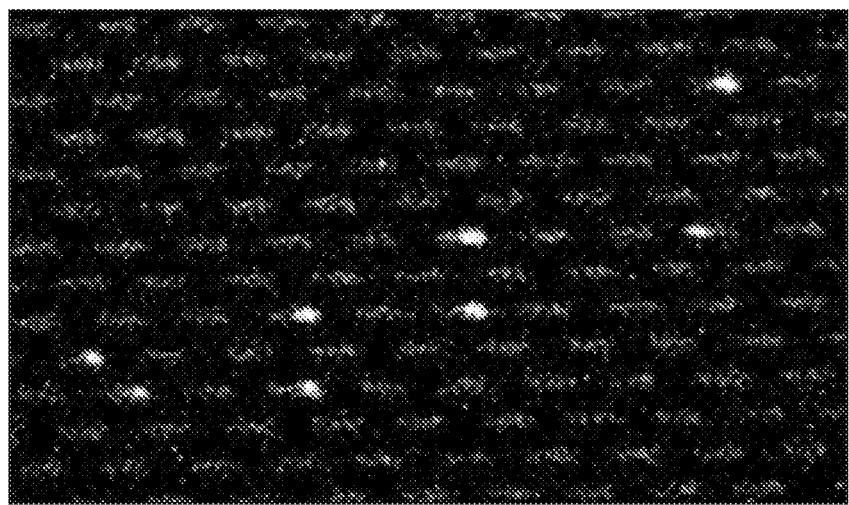
FIG. 11A shows an image of the beads in respective wells before sealing and FIG. 11B shows an image a few minutes after sealing.
Figure 11B:
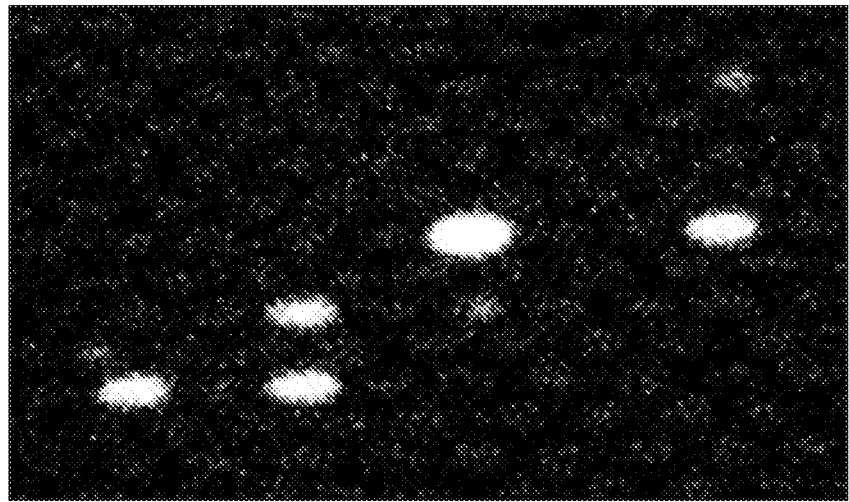

Arrays of bead wells 10a with slit geometry (e.g., FIGS. 2A, 2B) were also tested in ELISA assays based upon the Single Molecule Arrays (SiMoA) format popularized by Tufts University and Quanterix Corporation to determine if decoupling the bead background fluorescence (which can be significant and variable) from the assay signal could provide signal to noise enhancement for unmistakable determination of positive reactions. FIGS. 11A/11B show an example where beads labeled with anti-TNF-α antibodies were used to capture TNF-α antigen. Biotinylated secondary antibodies for the antigen were used to attach a streptavidin-conjugated β-galactosidase enzyme molecule to the antigen captured by the bead. The beads were loaded into the array and sealed with a fluorogenic substrate for the enzyme label. FIG. 11A shows an image of the beads before sealing and FIG. 11B shows an image a few minutes later. In FIG. 11A, beads in wells (8) can be seen by background fluorescence before sealing and in FIG. 11B the assay readout is unequivocal, showing 5 positives.

In five (5) of the wells containing beads, a clear signal can be seen in the assay region of the wells, and three (3) wells containing beads show only background fluorescence. The ability to unambiguously call positive reactions may improve accuracy for the SiMoA assays by removing the contribution of bead background fluorescence and eliminating the need to image the array before significant conversion of the substrate takes place (time zero or $T_0$ images). Since the reaction occurs very quickly, taking $T_0$ images of large arrays may not be feasible if the imaging system lacks sufficient resolution or field of view to cover the entire array in one or a few images. By reading the assay signal in a separate region, the array can be scanned after the reaction has occurred, and multiple images can be stitched together or otherwise interrogated or combined to create an image of the entire array without loss of accuracy. Additionally, greater reagent volume in bead wells accommodated by embodiments of the new well geometries means more substrate molecules and thus more potential fluorophores can be obtained for each reaction.

Figure 12B:
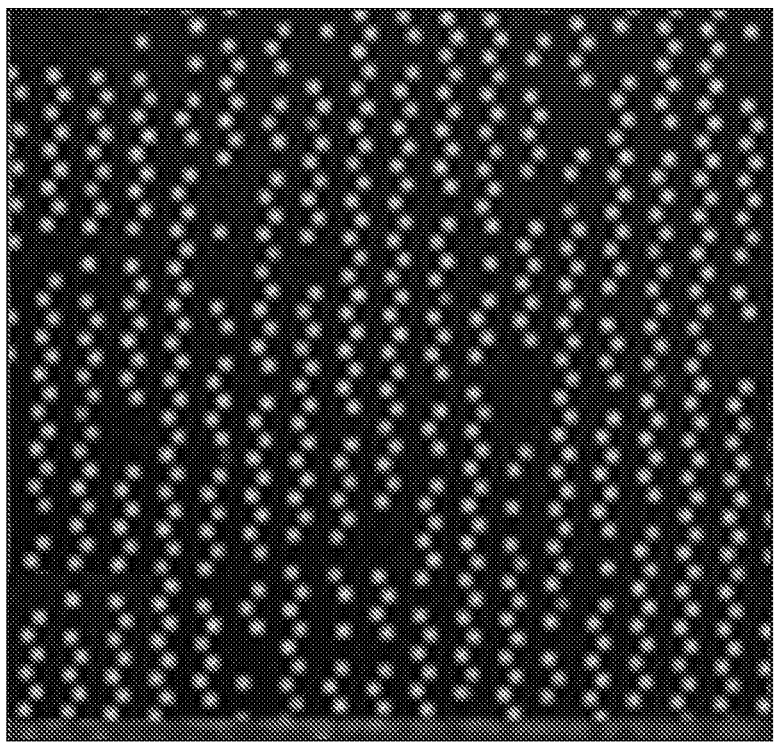
FIGS. 12A and 12B show an example of a polymer device with a bead well array which was fabricated by injection molding and loaded with beads. An SEM of the device with beads is shown in FIG. 12A and a fluorescence microscopy image of a loaded array is shown in FIG. 12B.
Figure 12A:
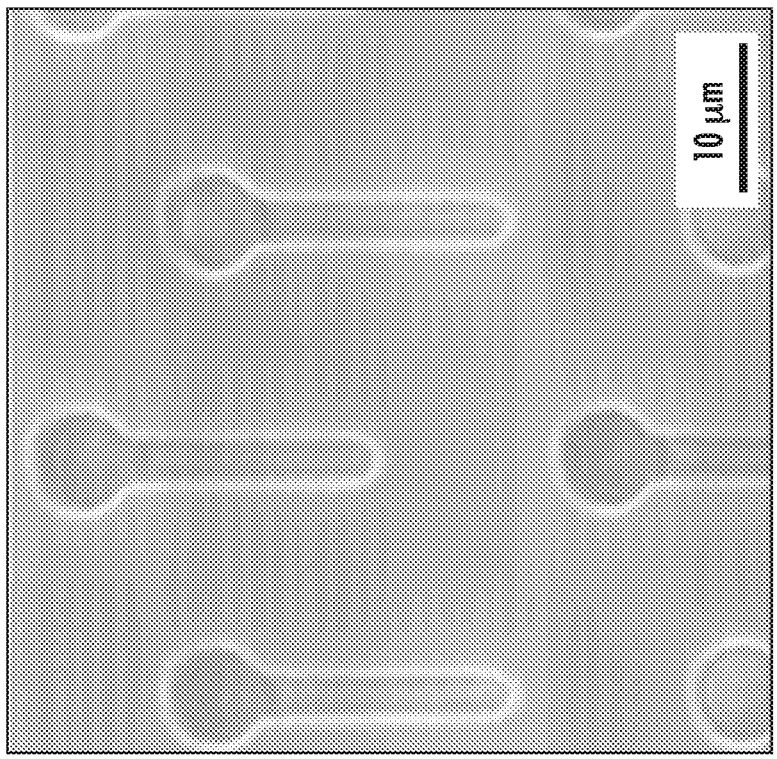

Fabrication of arrays 10a containing these well geometries with the shapes with a bead retention segment 11 and a signal detection segment 15 can be achieved in any suitable material, and is not limited to silicon or glass. For example, polymer substrates with well arrays 10a can be fabricated using methods such as hot embossing or injection molding. FIGS. 12A and 12B show an example of a polymer device with a bead well array 10a which was fabricated by injection molding and loaded with beads. An SEM of the device with beads is shown in FIG. 12A, and a fluorescence microscopy image of a loaded array is shown in FIG. 12B.

FIGS. 13A and 13B are SEM images showing an array fabricated with hot embossing using DRIE etched silicon mold (FIG. 13A) to fabricate bullseye-shaped wells in plastic/polymeric substrates. FIG. 13A also shows a 4° tapered non-cylindrical mold containing a 2 µm internal diameter annulus and FIG. 13B shows the corresponding plastic/polymeric replica.

Embodiments of the invention comprise reaction wells 10' with geometries configured to contain more than one bead so that a reaction between reagents released from one or more beads and reacting in solution or upon the surface of one or more beads or any combination thereof can be studied at a designated detection region(s) as shown or alternatively upon a bead's surface, for example, in FIGS. 14A-14D and 15A-15C. The bead well arrays 10a can include variations where some wells 10 hold one bead 25, some wells 10' hold two beads 25, and some wells 10' hold more than two beads 25 on a single substrate or fluidic device or on separate substrates or devices. Where a well 10' includes more than one bead retention segment 11, a plurality (typically each) of bead retention segments 11 can be in fluid communication with each other via a signal detection segment such as a fluidic channel 15ch.

FIGS. 14A-14D and 15A-15C show a few exemplary configurations that may exploit the ability to rapidly generate multiple replicates of combinations of mixture in a simple process that greatly reduces user interaction and labor compared to other combinatorial approaches that require the user to add liquid reagents for each component studied. These wells 10' can be designed to have two or more bead retention segments 11a and 11b and optionally 11c (FIGS. 15A-15C) to load two or more beads 25 (shown by way of example in FIG. 14D) with separate read-out/detection segments or regions 15 (typically thinner in width and/or depth regions) fluidly connected by a channel 15c. The bead well retention segments 11a, 11b (11c) can be the same or different sizes as shown. Iterations with additional shapes or numbers of beads are possible. While two and three bead retention segments are shown, the wells 10' can be configured with more than three bead retention segments 11 and may have a different geometry.

Use of the bead wells 10, 10' contemplated by embodiments of the invention is not limited to PCR or ELISA-based assays. The arrays 10a can be used for any process or method where it may be beneficial to spatially separate a bead carrying a reagent or analyte from a volume of reagent and the area or region where a corresponding signal is measured and/or detected.

In some embodiments, the new bead wells 10 can be used in methods to reduce the tediousness and expense required for testing different primer sets to assess their compatibility in multiplexed reactions. Complex predictive software exists to analyze and suggest PCR primers using various guidelines to promote primer specificity and avoid the formation of primer dimers; however, current state-of-the-art software can only provide suggested sequences that must be empirically tested in pilot PCR experiments. This cycle of prediction, testing, and re-design is a very common problem among experimentalists, and is costly in both resources and time. Unpredicted primer dimers or off-target amplification results from various mechanisms, including non-canonical base interactions, poor enzyme fidelity, primer sequence mismatches that are ignored by the polymerase, and the presence of SNP sequences or unexpected experimental sequences. This process is even more complex in multiplex PCR reactions, especially so with samples containing nucleic acids from multiple organisms.

Primer dimer formation can significantly reduce the efficiency of PCR reactions and lead to false positives, confound sequencing efforts, and/or other downstream analysis of amplicons. Traditionally, primer sets must be mixed in different combinations to determine if two or more pairs interact with one another to form unintended amplicons (dimers). If many sets need to be integrated into a single reaction (for example, 10-50 sets), testing can require thousands of reactions for both the initial screening as well as retesting of the sets modified to reduce nonspecific products. If multiple encoded bead sets are made, each with a different primer set, they can be mixed together and loaded onto a device as a single aliquot instead of individually pipetted reagent solutions. If the beads are loaded into a microwell array 10 with reaction well geometries 10' that capture two or more beads 25 (FIGS. 14A-14C, 15A-15C, for example), a stochastic mixing of primer sets can be readily achieved. PCR can then reveal the presence of undesirable interactions between every combination of primer sets after decoding the array to determine the identity of each bead in each reaction. As there can be millions of these reaction wells in a single device, there will be many replicates of all possible combinations, providing a rich data set for analysis.

In a similar embodiment, screening multiple primer sets against different reference genomes can be done using arrays that load more than a single bead. To establish target specificity for a primer set, it is important to screen primer sets against not only their intended target but also the nucleic acids of multiple organisms that could be present in a relevant sample. While sequence databases can be used to eliminate many possible interactions, empirical testing is still required as sequences are often incomplete and current state of the art algorithms are far from perfect. For example, host genomic DNA and multiple species of related bacteria and virus serotypes should be screened for each assay designed for pathogen quantification. If applied to microbiome studies, hundreds to thousands of different, sometimes very closely related, species may need to be compared. Reference genome beads can be made by fragmenting an organism's genome and attaching the fragments to encoded beads (using methods such as biotinylation of the fragments with subsequent incubation with encoded, streptavidin-functionalized beads). By mixing a library of encoded primer set beads with a library of encoded reference genome beads, researchers would be able to screen for both off-target amplification and verify amplification efficiency for their intended target in a single assay. Primer beads can be efficiently combined with genome beads by using smaller beads for primers and larger beads for the genome (or vice versa). In this case, the reactions wells could contain a large bead well and a small bead well, connected by a narrow slit (FIG. 9B). If the larger genome beads are loaded into the large bead wells first, the smaller bead wells will be unoccupied. Following this step, smaller primer beads can be efficiently loaded into the smaller bead wells. This methodology may avoid undesirable primer-primer and genome-genome combinations in reaction wells. In this methodology, and others, it is not necessary that both reagents be released from the beads as the reference genome beads can, but do not necessarily need to, retain their reagents while the primers released from the beads interact with them and create a measureable signal in the detection region.

In another example, this principle can be applied to the nucleic acid profiling of many clinical or laboratory samples simultaneously. Sequences of nucleic acids such as mRNAs or lncRNAs from a single organism can be captured on a single bead set. A library can then be generated by combining differently encoded beads made from nucleic acid extractions from many different individuals. This library can then be screened for targets against a primer bead library as described above to identify single nucleotide polymorphisms (SNPs), gene expression, or other phenomenon.

Kits useful for carrying out the methods of the present invention can, in general, comprise one or more sets of beads having reagents attached thereto and other reagents for carrying out the methods as described above, such as restriction enzymes, optionally packaged with suitable instructions for carrying out the methods. The kits may also include containers for housing elements included therein. Such containers include, but are not limited to vials, microfluidic chips with bead well arrays and cartridges, including pre-loaded bead devices.

In some embodiments, the beads 25 may have primers attached thereto. The primers may be a pair of biotinylated primers, and the beads 25 may be streptavidin-labeled such that binding of the biotinylated primers to the beads occurs. In some embodiments, the beads 25 may include a marker, such as an optical marker, that may be used during analysis to identify the primers anchored to the respective beads 25. For example, different encoded beads of the same or different sizes may be marked for identification of different attached primer sets during analysis. Various pre-encoding methods may be used to provide a marker on the beads 25, including a predefined size, shape, magnetic property and/or fluorescence doping used alone or in combination with other encoding methods. Both custom-sequence biotinylated primers and streptavidin labeled paramagnetic magnetic beads can be readily purchased from commercial vendors or made in a suitable quantity in an appropriately equipped laboratory.

As noted above, although embodiments according to the present invention are also described herein with respect to PCR reactions, it should be understood that the microfluidic devices, beads and reaction methods described herein may be used in various other reactions, e.g., where reagents are cleaved from a bead into a well to participate in a reaction. For example, any nucleic acid transcription and/or amplification-related reaction or sequencing reaction is within the scope of the current invention, including but not limited to PCR reactions, real-time PCR (rt-PCR), digital PCR (dPCR), reverse transcription of RNA into cDNA (RT), PCR of cDNA from previous RT step (RT-PCR), RT-PCR using real-time or digital quantification, immuno-PCR (iPCR) and its variants, loop-mediated isothermal amplification (LAMP), rolling circle replication, and/or non-enzymatic nucleic acid amplification methods (e.g., "DNA circuits"). Other reactions that are included within the scope of the present invention include but are not limited to enzyme-linked immunosorbent assays (ELISA), single molecule array (SiMoA) or digital ELISAs, ELISAs where the fluorogenic substrate is bound to the support surface to be cleaved at some point for subsequent reaction, reactions in which multiple beads are used to deliver different reagents for combinatorial chemistry, reactions where the beads deliver a catalyst reagent, and/or reactions where "click" chemistry reagents are delivered in stoichiometries determined by stochastic bead loading.

Figure 16:
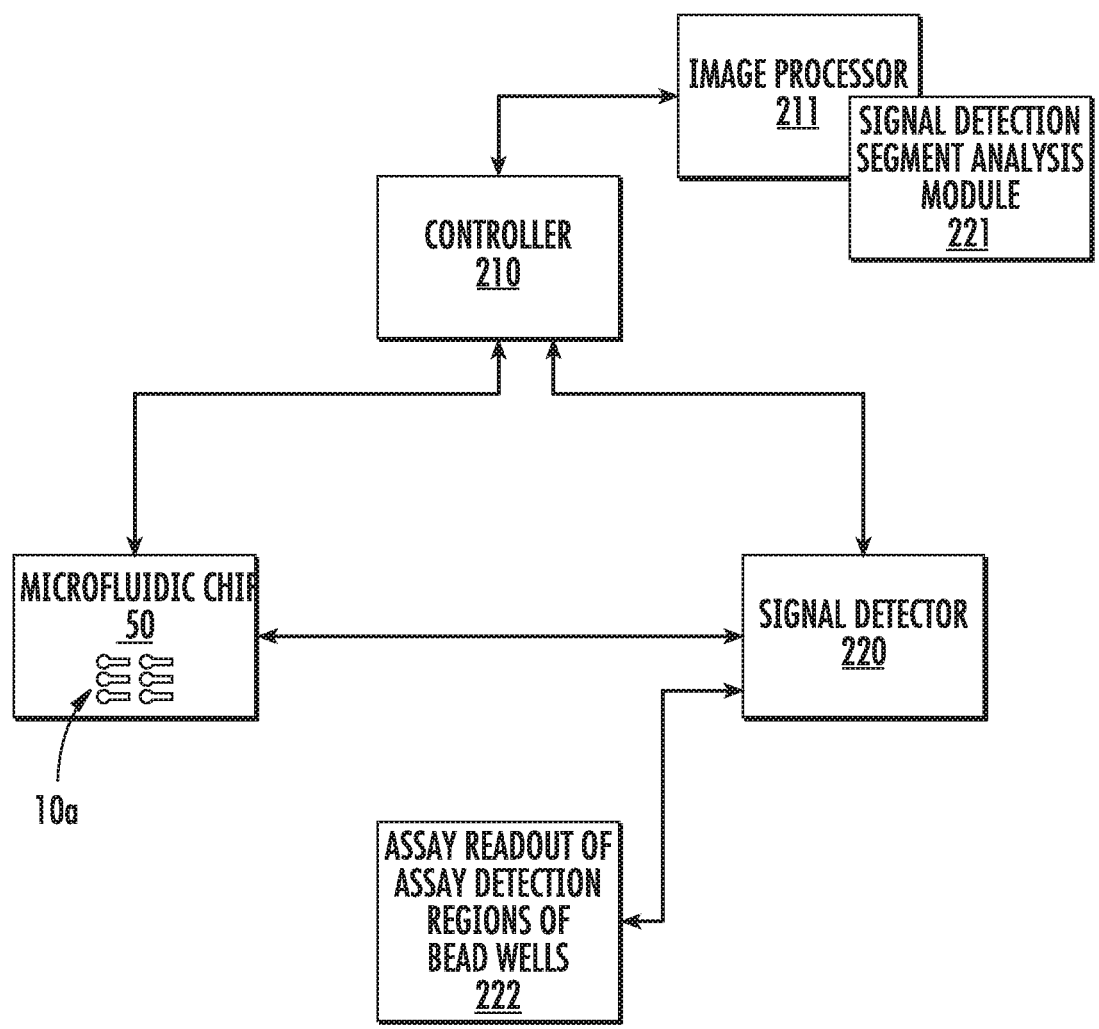
FIG. 16 is a schematic illustration of an analysis system according to embodiments of the present invention.

FIG. 16 is a schematic illustration of an analysis system 200. The system 200 can include at least one controller 210 (typically comprising at least one processor) in communication with an electronic signal detector 220 such as an optical detector comprising a camera or other imaging device or other signal detection device. The signal detector 220 is configured to detect signal of the bead well array 10a of a respective microfluidic chip 50. The controller 210 can be in communication with an image processor 211 having a module 221 (e.g., computer program) configured to identify if an assay signal is present in signal detection segments of the reaction wells. The image processor module 221 can be totally or partially onboard or remote from the controller and/or signal detector 220. The image processor module 221 can be configured to combine a plurality of post-assay images of the wells to assess whether a well has a positive readout. The image processor module 221 may remove the background noise from the bead retention segment of respective wells. The module 221 may be configured to identify the presence of a signal from the detection segment(s) of a respective well to identify whether a positive assay reaction occurred.

Figure 17:
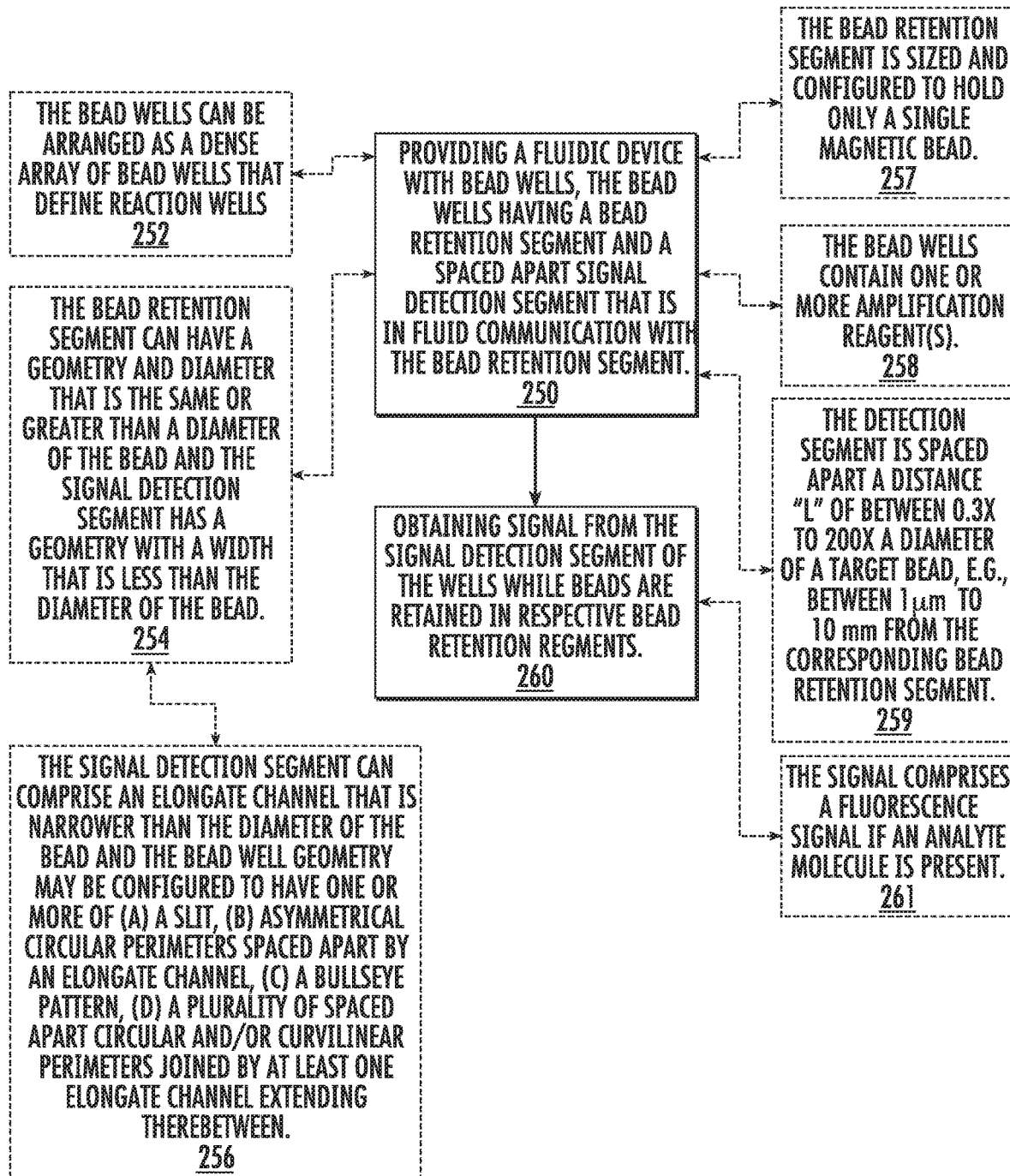
FIGS. 17-19 are flow charts representing exemplary methods of embodiments of the present invention.

FIG. 17 is a flow chart of exemplary operations that can be used to carry out analysis methods according to embodiments of the present invention. A fluidic device with bead wells is provided; the bead wells have a bead retention segment and a spaced apart signal detection segment that is in fluid communication with the bead retention segment (block 250). Signal is obtained from the signal detection segment of the wells while beads are retained in respective bead retention segments (block 260).

In these and/or other embodiments, an encoding signal can be read from the bead containing segment (i.e. directly from the bead) to ascertain what reagent(s) and/or analyte the bead may contain. In this manner, the array can be decoded to determine the meaning of a positive or negative assay signal. Beads may be optically encoded by means known to those skilled in the art, including fluorescent dye staining by one or more dyes at one or more intensity levels, bead diameter, bead shape, or any combination of defined and/or observable or detectable properties.

The bead wells can be arranged as a dense array of bead wells that define reaction wells (block 252). The bead retention segment can have a geometry and diameter that is the same or greater than a diameter of the bead and the signal detection segment has a geometry with a width that is less than the diameter of the bead (block 254).

The signal detection segment can comprise an elongate channel that is narrower than the diameter of the bead and the bead well geometry may be configured to have one or more of (a) a slit, (b) asymmetrical circular perimeters spaced apart by an elongate channel, (c) a bulls-eye pattern (i.e., an elongate channel merging into an annular channel), (d) a plurality of spaced apart circular and/or curvilinear perimeters joined by at least one elongate channel extending therebetween (block 256).

The bead retention segment can be sized and configured to hold only a single magnetic bead (block 257).

The bead wells can contain one or more amplification reagent(s) (block 258).

The detection segment can be spaced apart a distance L of between 0.3× and 200× the diameter of a target bead, e.g., between 1 µm to 1 mm or more, typically between 1-100 µm, from the corresponding bead retention segment (block 259).

The signal can include a fluorescence signal (with a tail) if an analyte molecule is present (block 261).

Figure 18:
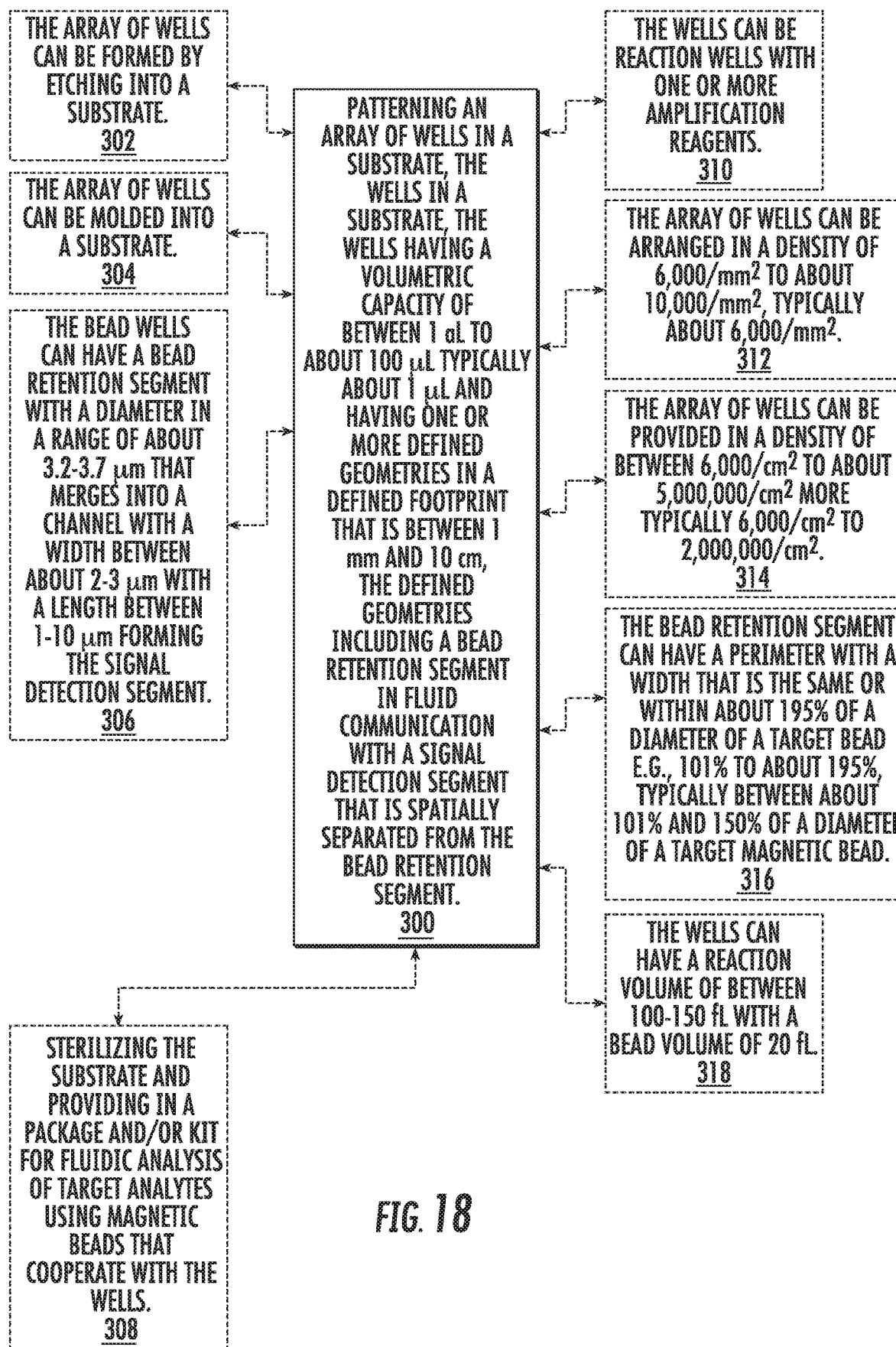

FIG. 18 is a flow chart of a method of fabricating exemplary devices according to embodiments of the present invention. An array of wells is patterned (e.g., formed) in a substrate; the wells can have a volumetric capacity of between 1 aL to 100 µL, more typically between 1 fL and 1 µL, and one or more defined geometries in a defined footprint with linear dimensions between 1 mm and 10 cm, the defined geometries including a bead retention segment in fluid communication with a signal detection segment that is spatially separated from the bead retention segment (block 300).

The array of wells can be formed by etching into a substrate (block 302).

The array of wells can be molded into a substrate (block 304). Other fabrication methods are contemplated, e.g., photolithography, FIB milling, embossing, stamping and the like.

The bead wells may have a bead retention segment with a diameter in a range of about 3.2-3.7 µm that merges into a channel with a width between about 2-3 µm with a length L of between 0.3× and 200× the diameter of a target bead, e.g., between 1 µm and 10 mm, between 1 µm and 1 mm, between 1-100 µm and/or between 1-10 µm, in some embodiments, forming the signal detection segment (block 306).

Sterilizing the substrate and providing in a package and/or kit for fluidic analysis of target analytes using magnetic beads that cooperate with the wells (block 308).

The wells can be reaction wells with one or more amplification reagents.

The array of wells can be arranged in a density of 6000/mm$^2$ to about 10,000/mm$^2$, typically about 6,000/mm$^2$ (block 312).

The array of wells can be provided in a density of between 10,000/cm$^2$ to about 2,000,000/cm$^2$ (block 314).

The bead retention segment can have a perimeter with a width that is the same or within about 195% of a diameter of a target (e.g., magnetic) bead, i.e., between 101% and 195% or 150% of the diameter of a target bead (block 316).

The wells can have a reaction volume of between 100-150 fL with a bead volume of 20 fL (block 318).

Figure 19:
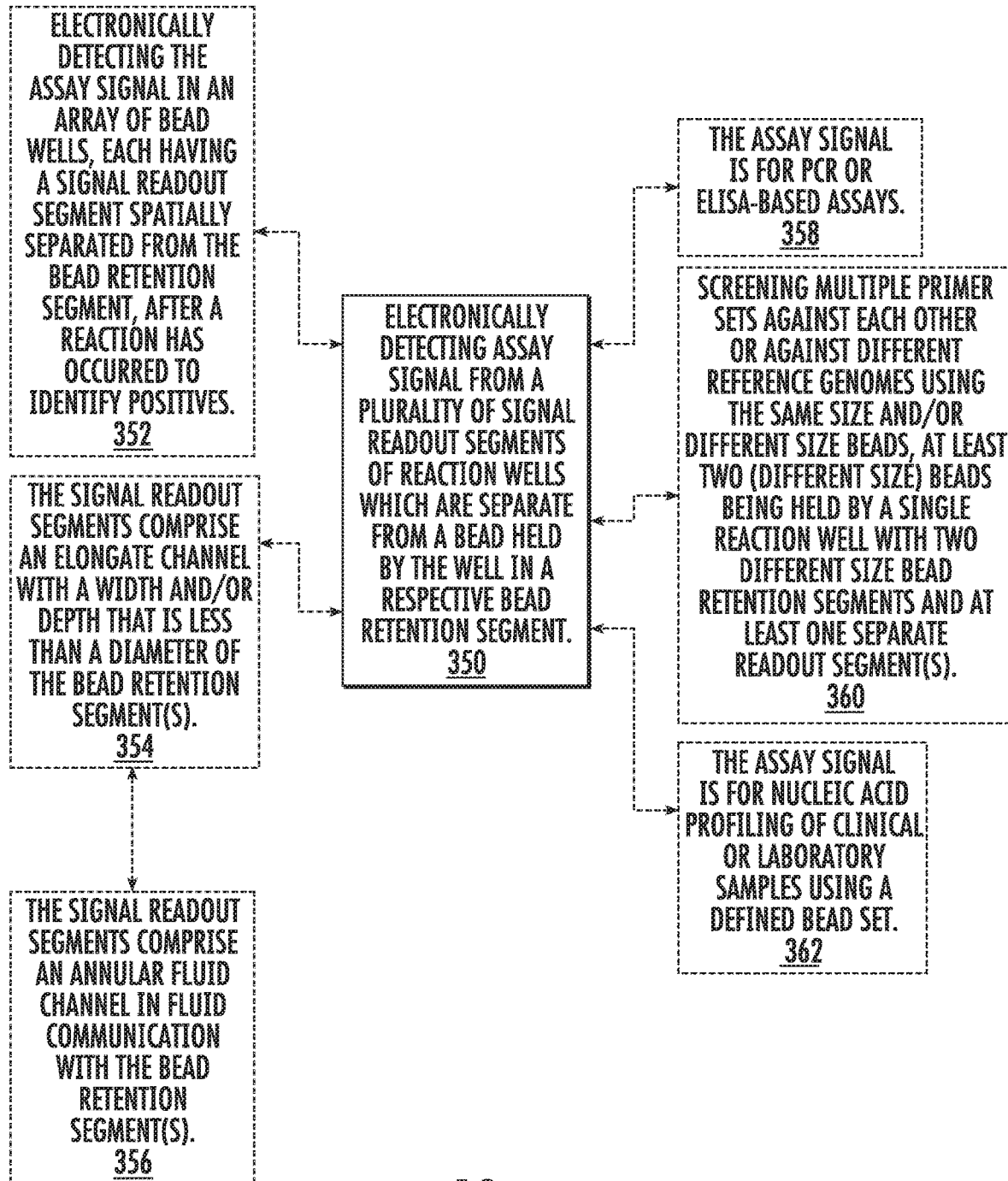

FIG. 19 is a flowchart of a method of evaluating an assay according to embodiments of the present invention. Assay signal is electronically detected from a plurality of signal readout segments of reaction wells, which are separate from a bead held by the well in a respective bead retention segment (block 350). The term "electronically" refers to all founts of machine-based detection (not human vision) such as a camera, e.g., a CCD camera, a SEM, and the like. The signal can be an increase in intensity, fluorescence, one or more defined colors, a defined pixel parameter and the like, including a change in light scattering properties (transparence), a change in transmittance or absorbance, chemiluminescence or combinations of different parameters.

The assay signal can be electronically detected from an array of bead wells, each having a signal readout segment spatially separated from the bead retention segment, after a reaction has occurred to identify positives (block 352).

The signal readout segments comprise an elongate channel with a width and/or depth that is less than a diameter of the bead retention segment(s) (block 354).

The signal readout segments comprise an annular fluid channel in fluid communication with the bead retention segment(s) (block 356).

The assay signal is for a PCR or ELISA-based assays (block 358).

Multiple primer sets can be screened against each other or against different reference genomes using the same size beads or different size beads, at least two beads being held by a single reaction well with two (optionally different size) bead retention segments and at least one separate readout segment(s)(block 360).

The assay signal can be for nucleic acid profiling of clinical or laboratory samples using a defined bead set (block 362).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A fluidic device comprising:
    a plurality of reaction wells that are in fluid isolation from each other and sealed from one another by a sealing agent, and characterized in that each reaction well has at least one bead retention segment and at least one spatially separated signal detection segment that is configured as at least one elongate channel in fluid communication with the at least one bead retention segment, wherein the at least one bead retention segment has a depth direction, wherein the at least one elongate channel extends away from the at least one bead retention segment in a length direction that is perpendicular to the depth direction, and wherein the at least one elongate channel has a length in the length direction that is greater than a width of the at least one bead retention segment; and
    a plurality of magnetic beads, wherein one magnetic bead of the plurality of magnetic beads is physically retained in each bead retention segment of the plurality of reaction wells.

2. The device of claim 1, wherein the at least one elongate channel has a width that is less than the width of an adjacent bead retention segment.

3. The device of claim 1, wherein the at least one bead retention segment of at least some of the plurality of reaction wells consists of a single bead retention segment.

4. The device of claim 1, wherein the at least one bead retention segment is a plurality of bead retention segments.

5. The device of claim 1, wherein at least one of the plurality of reaction wells is configured so that the at least one bead retention segment is a plurality of bead retention segments with at least one neighboring pair of bead retention segments being spaced apart by the at least one elongate channel and with the at least one elongate channel fluidly connecting a corresponding neighboring pair of bead retention segments, and wherein the at least one elongate channel has a width that is narrower or a depth that is shallower or a width that is narrower and a depth that is shallower than that of the corresponding neighboring pair of bead retention segments.

6. The device of claim 1, wherein the at least one bead retention segment is a plurality of bead retention segments having a common size.

7. The device of claim 1, wherein the at least one bead retention segment is a plurality of bead retention segments, at least one of which has a different size from at least another one.

8. The device of claim 1, wherein the at least one bead retention segment and the at least one signal detection segment of each of the reaction wells comprise tapered and/or straight walls formed into a first planar substrate of the device.

9. The device of claim 1, wherein one or more of the at least one elongate channel comprises an annular fluid channel at an end portion thereof that is spaced a distance apart from the at least one bead retention segment and in fluid communication with the at least one bead retention segment.

10. The device of claim 1, wherein at least one of the reaction wells is configured with first and second bead retention segments as the at least one bead retention segment, wherein the first and second bead retention segments are spaced apart and fluidly connected by a straight fluid channel that defines the at least one elongate channel, wherein the straight fluid channel has a narrower width than the width of the first and second bead retention segments, and wherein the first and second bead retention segments have a circular perimeter.

11. The device of claim 10, wherein the first bead retention segment is larger or smaller in diameter and/or depth compared to the second bead retention segment.

12. A method for analyzing an analyte using the device of claim 1 by electronically detecting a signal from the at least one signal detection segment of the plurality of reaction wells, wherein reagents and/or analytes released from the beads held in respective bead retention segments diffuse through a common solution volume of respective reaction wells, and wherein the signal is detected from a signal detection segment of the at least one signal detection segment while the target beads are held in the respective bead retention segments with the signal detection segment of the at least one signal detection segment generating an optical signal comprising a tail that is distinguishable from a background signal of the corresponding bead.

13. The method of claim 12, wherein the signal comprises a fluorescence signal.

14. The method of claim 12, wherein electronically detecting the signal is carried out for an array in which one or more of the plurality of reaction wells comprise a different type of bead from one or more other ones of the plurality of reaction wells, each type of bead encoded with a unique signature and each type of bead functionalized with a different reagent for allowing detection of different analytes or different chemical reactions or different analytes and different chemical reactions.

15. A fluidic device comprising:
    a plurality of reaction wells characterized in that each reaction well has at least one bead retention segment and at least one spatially separated signal detection segment that is configured as at least one elongate channel in fluid communication with the at least one bead retention segment, wherein the at least one bead retention segment has a depth direction, wherein the at least one elongate channel extends away from the at least one bead retention segment in a length direction that is perpendicular to the depth direction, and wherein the at least one elongate channel has a length in the length direction that is greater than a width of the at least one bead retention segment,
    wherein the device is a microfluidic chip and the plurality of reaction wells are provided as an array of reaction wells, wherein the at least one bead retention segment and the at least one signal detection segment reside in a first planar substrate with the first planar substrate defining an open upper surface and sidewalls of the at least one bead retention segment and the at least one signal detection segment, and wherein the device further comprises a second planar substrate that couples to the first planar substrate and defines a closed outer surface with at least one fluid port.

16. The device of claim 15, wherein each bead retention segment of the plurality of reaction wells is sized and configured to hold only a respective single bead with a diameter in a range of about 10 nm to about 1 mm, and wherein at least one of the plurality of reaction wells has a single bead retention segment as the at least one bead retention segment that merges into a separate corresponding single elongate channel as the at least one signal detection segment, and wherein the separate corresponding single elongate channel has a width that is narrower than the width of the bead retention segment and has an end portion that resides a distance L in the length direction in a range of 1 μm to 1 mm from the single bead retention segment.

17. The device of claim 15, wherein the at least one bead retention segment is sized and configured to hold a microspherical bead with a diameter in a range of 100 nm to 1 mm, and wherein the width of the at least one bead retention segment is in a range of 101% to 195% of the diameter of a respective bead held therein.

18. A fluidic device comprising:
a plurality of reaction wells characterized in that each reaction well has at least one bead retention segment and at least one spatially separated signal detection segment that is configured as at least one elongate channel in fluid communication with the at least one bead retention segment, wherein the at least one bead retention segment has a depth direction, wherein the at least one elongate channel extends away from the at least one bead retention segment in a length direction that is perpendicular to the depth direction, and wherein the at least one elongate channel has a length in the length direction that is greater than a width of the at least one bead retention segment,
wherein each of the plurality of reaction wells has a volumetric capacity in a range of 1 aL to 1 μL, and wherein the device further comprises a sealing agent that seals the plurality of reaction wells from each other.

19. A fluidic device comprising:
a first substrate comprising a plurality of reaction wells characterized in that each reaction well has at least one bead retention segment and at least one spatially separated signal detection segment that is configured as at least one elongate channel in fluid communication with the at least one bead retention segment, wherein the at least one bead retention segment has a depth direction, wherein the at least one elongate channel extends away from the at least one bead retention segment in a direction that is perpendicular to the depth direction, wherein a volume capacity of each reaction well is in a range of 1 aL to 100 μL, wherein the device further comprises a spacer and a sealing agent between the first substrate and a second substrate, wherein each reaction well of the plurality of reaction wells comprises a reaction solution that does not touch the second substrate, and wherein the plurality of reaction wells are sealed from one another by the sealing agent.

20. A fluidic device comprising:
a plurality of reaction wells characterized in that each reaction well has at least one bead retention segment and at least one spatially separated signal detection segment that is configured as at least one elongate channel in fluid communication with the at least one bead retention segment, wherein the at least one bead retention segment has a depth direction, wherein the at least one elongate channel extends away from the at least one bead retention segment in a length direction that is perpendicular to the depth direction, and wherein the at least one elongate channel has a length in the length direction that is greater than a width of the at least one bead retention segment,
wherein the reaction wells are provided in a density in a range of about 6,000 wells/cm$^2$ to about 2,000,000 wells/cm$^2$.

* * * * *

UNITED STATES PATENT AND TRADEMARK OFFICE
CERTIFICATE OF CORRECTION

| | | |
|---|---|---|
| PATENT NO. | : 10,870,111 B2 | Page 1 of 1 |
| APPLICATION NO. | : 15/742616 | |
| DATED | : December 22, 2020 | |
| INVENTOR(S) | : Ramsey et al. | |

It is certified that error appears in the above-identified patent and that said Letters Patent is hereby corrected as shown below:

In the Specification

Column 13, Line 21: Please correct "units/4" to read -- units/µL --

Column 13, Line 30: Please correct "≈3 µM" to read -- ≈3 pM --

Signed and Sealed this
Twentieth Day of April, 2021

Drew Hirshfeld
*Performing the Functions and Duties of the
Under Secretary of Commerce for Intellectual Property and
Director of the United States Patent and Trademark Office*